US009205077B2

(12) United States Patent
Hübsch et al.

(10) Patent No.: US 9,205,077 B2
(45) Date of Patent: Dec. 8, 2015

(54) 2-ALKOXY-SUBSTITUTED DICYANOPYRIDINES AND THEIR USE

(71) Applicant: Bayer Intellectual Property GmbH, Monheim (DE)

(72) Inventors: Walter Hübsch, Wuppertal (DE); Daniel Meibom, Leverkusen (DE); Alexandros Vakalopoulos, Hilden (DE); Barbara Albrecht-Küpper, Wülfrath (DE); Peter Nell, Wuppertal (DE); Katja Zimmermann, Düsseldorf (DE); Frank Süßmeier, München (DE); Joerg Keldenich, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/304,801

(22) Filed: Jun. 13, 2014

(65) Prior Publication Data

US 2014/0296295 A1 Oct. 2, 2014

Related U.S. Application Data

(62) Division of application No. 12/995,028, filed as application No. PCT/EP2009/003652 on May 22, 2009, now Pat. No. 8,791,146.

(30) Foreign Application Priority Data

May 29, 2008 (DE) .......................... 10 2008 025 841

(51) Int. Cl.
| | | |
|---|---|---|
| C07D 413/12 | (2006.01) |
| A61K 31/44 | (2006.01) |
| C07D 213/70 | (2006.01) |
| C07D 417/12 | (2006.01) |
| C07D 417/14 | (2006.01) |
| A61K 31/4439 | (2006.01) |
| A61K 31/444 | (2006.01) |
| A61K 45/06 | (2006.01) |
| C07D 213/85 | (2006.01) |
| C07D 401/12 | (2006.01) |

(52) U.S. Cl.
CPC ............... *A61K 31/44* (2013.01); *A61K 31/444* (2013.01); *A61K 31/4439* (2013.01); *A61K 45/06* (2013.01); *C07D 213/70* (2013.01); *C07D 213/85* (2013.01); *C07D 401/12* (2013.01); *C07D 413/12* (2013.01); *C07D 417/12* (2013.01); *C07D 417/14* (2013.01)

(58) Field of Classification Search
CPC ..................................................... C07D 413/12
USPC ........................................ 546/271.4; 514/340
See application file for complete search history.

(56) References Cited

U.S. PATENT DOCUMENTS 8,440,700 B2 * 5/2013 Nell et al. ..................... 514/340

OTHER PUBLICATIONS

Guillory (in Brittain ed.), "Polymorphism in Pharmaceutical Solids.," NY: Marcel Dekker, Inc., 1999, 1-2, 125-181, 183-226.*
Yu et al., "Physical characterization of, etc.," PSTT, vl. 1(3), 118-127 (1998).*
Vippagunta et al., "Crystalline Solids", Advanced Drug Delivery Reviews 48 (2001) 3-26.*

* cited by examiner

*Primary Examiner* — Patricia L Morris
(74) *Attorney, Agent, or Firm* — Karen B. King

(57) ABSTRACT

The present application relates to novel 2-alkoxy-substituted dicyanopyridines, to processes for their preparation, to their use for the treatment and/or prophylaxis of diseases and to their use for preparing medicaments for the treatment and/or prophylaxis of diseases, preferably for the treatment and/or prevention of cardiovascular disorders.

8 Claims, No Drawings

2-ALKOXY-SUBSTITUTED DICYANOPYRIDINES AND THEIR USE

The present application relates to novel 2-alkoxy-substituted dicyanopyridines, to processes for their preparation, to their use for the treatment and/or prophylaxis of diseases and to their use for preparing medicaments for the treatment and/or prophylaxis of diseases, preferably for the treatment and/or prevention of cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart against ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

In humans, activation of A1 receptors by specific A1 agonists leads to a frequency-dependent lowering of the heart rate, without any effect on blood pressure. Selective A1 agonists may thus be suitable inter alia for treating angina pectoris and atrial fibrillation.

The cardioprotective action of the A1 receptors in the heart may be utilized inter alia by activating these A1 receptors with specific A1 agonists for treatment and organ protection in cases of acute myocardial infarction, acute coronary syndrome, heart failure, bypass operations, heart catheter examinations and organ transplantations.

The activation of A2b receptors by adenosine or specific A2b agonists leads, via dilation of blood vessels, to lowering of the blood pressure. The lowering of the blood pressure is accompanied by a reflectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In adipocytes, the activation of A1 and A2b receptors leads to an inhibition of lipolysis. Thus, the selective or combined action of A1 and A1/A2b agonists on lipid metabolism results in a lowering of free fatty acids and triglycerides. In turn, in patients suffering from metabolic syndrome and in diabetics, reducing lipids leads to lower insulin resistance and improved symptoms.

In humans, the inhibition of A1 receptors by specific A1 antagonists has a uricosuric, natriuretic and potassium-sparing diuretic effect without affecting the glomerular filtration rate, thus being renoprotective. Accordingly, selective A1 antagonists can be suitable inter alia for treating acute heart failure and chronic heart failure. Furthermore, they can be used for renoprotection in cases of nephropathy and other renal disorders.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference).

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of these adenosine ligands known from the prior art have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous administration.

WO 01/25210, WO 02/070484 and WO 02/070485 disclose substituted 2-thio- and 2-oxy-3,5-dicyano-4-phenyl-6-aminopyridines as adenosine receptor ligands for the treatment of cardiovascular disorders. WO 03/053441 describes specific substituted 2-thio-3,5-dicyano-4-phenyl-6-aminopyridines as selective ligands of the adenosine A1 receptor for the treatment of cardiovascular disorders. However, it has been found that these compounds have disadvantages with respect to their physicochemical properties such as, for example, their solubility and/or formulatability, and/or with respect to their in vivo properties, such as, for example, their pharmacokinetic behaviour, their dose-activity relationship and/or their metabolic path.

The preparation of substituted 2-thiopyridines is described in WO 98/54139. WO 99/32117 discloses substituted pyridines as acetylcholine receptor modulators for the treatment of CNS disorders. Furthermore, WO 01/62233 claims various pyridine and pyrimidine derivatives and also their use as adenosine receptor modulators. Substituted 3,5-dicyanopyridines as calcium-dependent potassium channel openers for the treatment of urological disorders are disclosed in EP 1 302 463-A1. WO 03/091246 describes pyrrole-substituted pyridines and pyrimidines as kinase inhibitors for the treatment of cancer, for example. WO 2008/008059 describes the use of various heterocyclic compounds for the treatment of cancer. WO 2009/015776 discloses oxazole-substituted dicyanopyridines for treating cardiovascular disorders.

It is an object of the present invention to provide novel compounds which act as potent and selective ligands of the adenosine A1 and/or A2b receptor and as such are suitable for the treatment and/or prevention of diseases, in particular for the treatment and/or prevention of cardiovascular disorders and have an identical or improved physicochemical, pharmacokinetic and/or therapeutic profile compared to the compounds known from the prior art.

The present invention provides compounds of the formula (I)

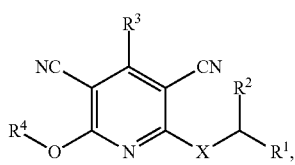

in which
X represents O or S,
$R^1$ represents $(C_6-C_{10})$-aryl or 5- to 10-membered heteroaryl,
where $(C_6-C_{10})$-aryl and 5- to 10-membered heteroaryl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, $(C_3-C_7)$-cycloalkylaminocarbonyl, aminosulphonyl, mono-$(C_1-C_6)$-alkylaminosulphonyl, di-$(C_1-C_6)$-alkylaminosulphonyl, $(C_1-C_6)$-alkylsulphonylamino, pyrrolidino, piperidino, morpholino, piperazino, N'—$(C_1-C_4)$-alkylpiperazino, pyrrolidinocarbonyl, piperidinocarbonyl, morpholinocarbonyl, piperazinocarbonyl, N'—$(C_1-C_4)$-alkylpiperazinocarbonyl and -L-$R^5$,
in which
L represents a bond, NH or O,
$R^5$ represents phenyl or 5- or 6-membered heteroaryl,
where phenyl and 5- or 6-membered heteroaryl for their part may be substituted by 1 to 3 substituents independently of one another selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl,
$R^2$ represents hydrogen or $(C_1-C_4)$-alkyl,
$R^3$ represents phenyl or 5- or 6-membered heteroaryl,
where phenyl and 5- or 6-membered heteroaryl may be substituted by 1 to 3 substituents independently of one another selected from the group consisting of halogen, cyano, hydroxyl, $(C_1-C_6)$-alkyl, $(C_1-C_6)$-alkoxy, $(C_3-C_7)$-cycloalkoxy, tetrahydrofuranyloxy, pyrrolidinyloxy and —$NR^A R^B$,
where $(C_1-C_6)$-alkyl and $(C_1-C_6)$-alkoxy may be substituted by 1 to 3 substituents independently of one another selected from the group consisting of fluorine, trifluoromethyl, $(C_3-C_7)$-cycloalkyl, hydroxyl, $(C_1-C_4)$-alkoxy, hydroxycarbonyl, $(C_1-C_4)$-alkoxycarbonyl, amino, aminocarbonyl, mono-$(C_1-C_4)$-alkylamino and di-$(C_1-C_4)$-alkylamino,
and
where $(C_3-C_7)$-cycloalkoxy, tetrahydrofuranyloxy and pyrrolidinyloxy may be substituted by 1 or 2 substituents independently of one another selected from the group consisting of $(C_1-C_4)$-alkyl, hydroxyl, oxo and $(C_1-C_4)$-alkoxy,
and
where
$R^A$ represents hydrogen or $(C_1-C_6)$-alkyl,
where $(C_1-C_6)$-alkyl for its part may be substituted by 1 to 3 fluorine substituents,
and
where $(C_1-C_6)$-alkyl for its part may be substituted by a substituent selected from the group consisting of hydroxyl and $(C_1-C_4)$-alkoxy,
$R^B$ represents hydrogen, $(C_1-C_6)$-alkyl, $(C_3-C_7)$-cycloalkyl, $(C_1-C_6)$-alkylcarbonyl, $(C_1-C_4)$-alkylsulphonyl or $(C_3-C_7)$-cycloalkylsulphonyl,
where $(C_1-C_6)$-alkyl for its part may be substituted by 1 or 2 substituents independently of one another selected from the group consisting of fluorine, trifluoromethyl, $(C_3-C_7)$-cycloalkyl, hydroxyl, $(C_1-C_4)$-alkoxy, hydroxycarbonyl, $(C_1-C_4)$-alkoxycarbonyl, amino, mono-$(C_1-C_4)$-alkylamino and di-$(C_1-C_4)$-alkylamino,
and
where $(C_3-C_7)$-cycloalkyl for its part may be substituted by 1 or 2 substituents independently of one another selected from the group consisting of $(C_1-C_4)$-alkyl, hydroxyl, oxo and $(C_1-C_4)$-alkoxy,
or
$R^A$ and $R^B$ together with the nitrogen atom to which they are attached form a 4- to 7-membered heterocycle which may contain a further ring heteroatom from the group consisting of N, O and S and may be substituted by 1 or 2 substituents independently of one another selected from the group consisting of $(C_1-C_4)$-alkyl, hydroxyl, oxo and $(C_1-C_4)$-alkoxy,
or
where two adjacent substituents at phenyl together with the carbon atoms to which they are attached may form a 1,3-dioxolane, 1,3-dioxane or 2,2-difluoro-1,3-dioxolane, $R^4$ represents $(C_1-C_6)$-alkyl, $(C_3-C_7)$-cycloalkyl or 4- to 6-membered heterocyclyl, where $(C_1-C_6)$-alkyl may be substituted by 1 or 2 substituents independently of one another selected from the group consisting of fluorine, trifluoromethyl, $(C_3-C_7)$-cycloalkyl, hydroxyl, $(C_1-C_4)$-alkoxy, hydroxycarbonyl, $(C_1-C_4)$-alkoxycarbonyl, amino, mono-$(C_1-C_4)$-alkylamino, di-$(C_1-C_4)$-alkylamino, aminocarbonyl, mono-$(C_1-C_4)$-alkylaminocarbonyl, di-$(C_1-C_4)$-alkylaminocarbonyl and 5- or 6-membered heterocyclyl, where $(C_1-C_4)$-alkoxy may be substituted by 1 or 2 substituents independently of one another selected from the group consisting of hydroxyl and $(C_1-C_4)$-alkoxy and where 5- or 6-membered heterocyclyl may be substituted by a substituent selected from the group consisting of oxo and $(C_1-C_4)$-alkyl and where $(C_3-C_7)$-cycloalkyl and 4- to 6-membered heterocyclyl may be substituted by 1 or 2 substituents independently of one another selected from the group consisting of $(C_1-C_4)$-alkyl, hydroxyl, $(C_1-C_4)$-alkoxy, hydroxycarbonyl, $(C_1-C_4)$-alkoxycarbonyl, amino, mono-$(C_1-C_4)$-alkylamino and di-$(C_1-C_4)$-alkylamino, and N-oxides, salts, solvates, salts of the N-oxides and solvates of the N-oxides and salts thereof.

Compounds according to the invention are the compounds of the formula (I) and the N-oxides, salts, solvates, salts of the N-oxides and solvates of the salts and N-oxides thereof, the compounds which are encompassed by the formula (I) of the formulae mentioned below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

Alkyl is in the context of the invention a straight-chain or branched alkyl radical having 1 to 6 or 1 to 4 carbon atoms. A straight-chain or branched alkyl adical having 1 to 4 carbon atoms is preferred. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

Cycloalkyl is in the context of the invention a monocyclic saturated carbocycle having 3 to 7 or 5 or 6 ring carbon atoms. The following radicals may be mentioned by way of example and by way of preference: cyclopropyl, cyclobutyl, cyclopentyl, cyclohexyl and cycloheptyl.

Alkylcarbonyl is in the context of the invention a straight-chain or branched alkyl radical having 1 to 6 or 1 to 4 carbon atoms and a carbonyl group attached in position 1. The following radicals may be mentioned by way of example and by way of preference: methylcarbonyl, ethylcarbonyl, n-propylcarbonyl, isopropylcarbonyl, n-butylcarbonyl, isobutylcarbonyl and tert-butylcarbonyl.

Alkoxy is in the context of the invention a straight-chain or branched alkoxy radical having 1 to 6 or 1 to 4 or 2 to 4 carbon atoms. A straight-chain or branched alkoxy adical having 1 to 4 or 2 to 4 carbon atoms is preferred. The following radicals may be mentioned by way of example and by way of preference: methoxy, ethoxy, n-propoxy, isopropoxy, n-butoxy, tert-butoxy, n-pentoxy and n-hexoxy.

Cycloalkoxy is in the context of the invention a monocyclic saturated carbocycle having 3 to 7 carbon atoms which is attached via an oxygen atom. The following radicals may be mentioned by way of example and by way of preference: cyclopropyloxy, cyclobutyloxy, cyclopentyloxy, cyclohexyloxy and cycloheptyloxy.

Alkoxycarbonyl is in the context of the invention a straight-chain or branched alkoxy radical having 1 to 6 or 1 to 4 carbon atoms and a carbonyl group attached at the oxygen. A straight-chain or branched alkoxycarbonyl radical having 1 to 4 carbon atoms in the alkoxy group is preferred. The following radicals may be mentioned by way of example and by way of preference: methoxycarbonyl, ethoxycarbonyl, n-propoxycarbonyl, isopropoxycarbonyl and tert-butoxycarbonyl.

Monoalkylamino is in the context of the invention an amino group having a straight-chain or branched alkyl substituent having 1 to 6 or 1 to 4 carbon atoms. A straight-chain or branched monoalkylamino radical having 1 to 4 carbon atoms is preferred. The following radicals may be mentioned by way of example and by way of preference: methylamino, ethylamino, n-propylamino, isopropylamino, n-butylamino, tert-butylamino, n-pentylamino and n-hexylamino.

Dialkylamino is in the context of the invention an amino group having two identical or different straight-chain or branched alkyl substituents having 1 to 6 or 1 to 4 carbon atoms each. Straight-chain or branched dialkylamino radicals having 1 to 4 carbon atoms each are preferred. The following radicals may be mentioned by way of example and by way of preference: N,N-dimethylamino, N,N-diethylamino, N-ethyl-N-methylamino, N-methyl-N-n-propylamino, N-iso-propyl-N-n-propylamino, N,N-diisopropylamino, N-n-butyl-N-methylamino, N-tert-butyl-N-methylamino, N-ethyl-N-n-pentylamino and N-n-hexyl-N-methylamino.

Cycloalkylamino is in the context of the invention an amino group having a monocyclic saturated carbocycle having 3 to 7 carbon atoms. The following radicals may be mentioned by way of example and by way of preference: cyclopropylamino, cyclobutylamino, cyclopentylamino, cyclohexylamino and cycloheptylamino.

Monoalkylaminocarbonyl is in the context of the invention an amino group which is attached via a carbonyl group and has a straight-chain or branched alkyl substituent having 1 to 6 or 1 to 4 carbon atoms. A monoalkylaminocarbonyl radical having 1 to 4 carbon atoms in the alkyl group is preferred. The following radicals may be mentioned by way of example and by way of preference: methylaminocarbonyl, ethylaminocarbonyl, n-propylaminocarbonyl, isopropylaminocarbonyl, n-butylaminocarbonyl, tert-butylaminocarbonyl, n-pentylaminocarbonyl and n-hexylaminocarbonyl.

Dialkylaminocarbonyl is in the context of the invention an amino group which is attached via a carbonyl group and which has two identical or different straight-chain or branched alkyl substituents having 1 to 6 or 1 to 4 carbon atoms each. A dialkylaminocarbonyl radical having in each case 1 to 4 carbon atoms per alkyl group is preferred. The following radicals may be mentioned by way of example and by way of preference: N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl, N-tert-butyl-N-methylaminocarbonyl, N-n-pentyl-N-methylaminocarbonyl and N-n-hexyl-N-methylaminocarbonyl.

Cycloalkylaminocarbonyl is in the context of the invention an amino group which is attached via a carbonyl group and has a monocyclic saturated carbocycle having 3 to 7 carbon atoms. The following radicals may be mentioned by way of example and by way of preference: cyclopropylaminocarbonyl, cyclobutylaminocarbonyl, cyclopentylaminocarbonyl, cyclohexyl-aminocarbonyl and cycloheptylaminocarbonyl.

Monoalkylaminosulphonyl is in the context of the invention an amino group which is attached via a sulphonyl group and which has a straight-chain or branched alkyl substituent having 1 to 6 carbon atoms. The following radicals may be mentioned by way of example and by way of preference: methylaminosulphonyl, ethylaminosulphonyl, n-propylaminosulphonyl, isopropyl-aminosulphonyl, n-butylaminosulphonyl and tert-butylaminosulphonyl.

Dialkylaminosulphonyl is in the context of the invention an amino group which is attached via a sulphonyl group and which has two identical or different straight-chain or branched alkyl substituents having 1 to 6 carbon atoms each. The following radicals may be mentioned by way of example and by way of preference: N,N-dimethylaminosulphonyl, N,N-diethylaminosulphonyl, N-ethyl-N-methylaminosulphonyl, N-methyl-N-n-propylaminosulphonyl, N-n-butyl-N-methylaminosulphonyl and N-tert-butyl-N-methylaminosulphonyl.

Alkylsulphonyl is in the context of the invention a straight-chain or branched alkyl radical which has 1 to 4 carbon atoms and is attached via a sulphonyl group. The following radicals may be mentioned by way of example and by way of preference: methylsulphonyl, ethylsulphonyl, n-propylsulphonyl, isopropylsulphonyl, n-butylsulphonyl and tert-butylsulphonyl.

Cycloalkylsulphonyl is in the context of the invention a monocyclic saturated carbocycle which has 3 to 7 carbon atoms and is attached via a sulphonyl group. The following radicals may be mentioned by way of example and by way of preference: cyclopropylsulphonyl, cyclobutylsulphonyl, cyclopentylsulphonyl, cyclohexylsulphonyl and cycloheptylsulphonyl.

Alkylsulphonylamino is in the context of the invention an amino group having a straight-chain or branched alkylsulphonyl substituent which has 1 to 6 carbon atoms and which is attached via the sulphonyl group to the nitrogen atom. The following radicals may be mentioned by way of example and by way of preference: methylsulphonylamino, ethylsulphonylamino, n-propyl-sulphonylamino, isopropylsulphonylamino, tert-butylsulphonylamino, n-pentylsulphonylamino and n-hexylsulphonylamino.

Aryl is in the context of the invention an aromatic carbocycle having 6 or 10 ring carbon atoms. Preferred aryl radicals are phenyl and naphthyl.

Heterocyclyl is in the context of the invention a saturated heterocycle having a total of 4 to 7 ring atoms which contains one or two ring heteroatoms from the group consisting of N, O and S and is attached via a ring carbon atom or, if appropriate, via a ring nitrogen atom. The following radicals may be mentioned by way of example: azetidinyl, pyrrolidinyl, pyrazolidinyl, tetrahydrofuranyl, piperidinyl, piperazinyl, tetrahydropyranyl, morpholinyl and thiomorpholinyl. Azetidinyl, pyrrolidinyl, tetrahydrofuranyl, piperidinyl, piperazinyl, tetrahydropyranyl and morpholinyl are preferred.

Heteroaryl is in the context of the invention a monocyclic or optionally bicyclic aromatic heterocycle (heteroaromatic) which has a total of 5 to 10 ring atoms, contains up to three identical or different ring heteroatoms from the group consisting of N, O and S and is attached via a ring carbon atom or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to two ring heteroatoms from the group consisting of N, O and S, such as, for example, furyl, thienyl, thiazolyl, oxazolyl, isothiazolyl, isoxazolyl, pyrazolyl, imidazolyl, pyridyl, pyrimidinyl, pyridazinyl, pyrazinyl.

Halogen includes in the context of the invention fluorine, chlorine, bromine and iodine. Preference is given to chlorine or fluorine.

An oxo group is in the context of the invention an oxygen atom which is attached via a double bond to a carbon atom.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

In the context of the present invention, preference is given to compounds of the formula (I) in which X represents S, $R^1$ represents phenyl or 5- or 6-membered heteroaryl,
  where phenyl and 5- or 6-membered heteroaryl may be substituted by 1 or 2 substituents independently of one another selected from the group consisting of fluorine, chlorine, cyano, $(C_1-C_4)$-alkyl, trifluoromethyl, $(C_1-C_4)$-alkoxy, amino, mono-$(C_1-C_4)$-alkylamino, di-$(C_1-C_4)$-alkylamino, hydroxycarbonyl, $(C_1-C_4)$-alkoxycarbonyl, aminocarbonyl, mono-$(C_1-C_4)$-alkylaminocarbonyl, di-$(C_1-C_4)$-alkylaminocarbonyl, $(C_3-C_6)$-cycloalkylaminocarbonyl, $(C_1-C_4)$-alkylsulphonylamino, morpholino, piperazino, N'—$(C_1-C_4)$-alkylpiperazino and -L-$R^5$,
  in which
  L represents a bond or NH,
  $R^5$ represents phenyl or 5- or 6-membered heteroaryl,
    where phenyl and 5- or 6-membered heteroaryl for their part may be substituted by 1 or 2 substituents independently of one another selected from the group consisting of fluorine, chlorine, cyano, $(C_1-C_4)$-alkyl, trifluoromethyl, $(C_1-C_4)$-alkoxy, trifluoromethoxy, amino, hydroxycarbonyl and $(C_1-C_4)$-alkoxycarbonyl, $R^2$ represents hydrogen or methyl, $R^3$ represents phenyl, pyrrolyl, oxazolyl, thiazolyl, isoxazolyl, pyrazolyl, imidazolyl and pyridyl,
  where phenyl, pyrrolyl, oxazolyl, thiazolyl, isoxazolyl, pyrazolyl, imidazolyl and pyridyl may be substituted by 1 or 2 substituents independently of one another selected from the group consisting of fluorine, $(C_1-C_6)$-alkyl, hydroxyl, $(C_1-C_4)$-alkoxy and —$NR^AR^B$,
    where $(C_1-C_6)$-alkyl and $(C_1-C_4)$-alkoxy may be substituted by 1 to 3 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino,
    and
    in which
    $R^A$ represents hydrogen or $(C_1-C_4)$-alkyl,
      where $(C_1-C_4)$-alkyl for its part may be substituted by a substituent selected from the group consisting of hydroxyl and $(C_1-C_4)$-alkoxy,
    $R^B$ represents hydrogen or $(C_1-C_4)$-alkyl,
      where $(C_1-C_4)$-alkyl for its part may be substituted by 1 or 2 substituents independently of one another selected from the group consisting of hydroxyl, $(C_1-C_4)$-alkoxy and hydroxycarbonyl, $R^4$ represents $(C_1-C_6)$-alkyl, $(C_4-C_6)$-cycloalkyl or 5- or 6-membered heterocyclyl,
  where $(C_1-C_6)$-alkyl may be substituted by 1 or 2 substituents independently of one another selected from the group consisting of fluorine, trifluoromethyl, $(C_3-C_7)$-cycloalkyl, hydroxyl, methoxy, ethoxy, hydroxycarbonyl, methoxycarbonyl, ethoxycarbonyl, amino, methylamino, ethylamino, N,N-dimethylamino, N,N-diethylamino and 5- or 6-membered heterocyclyl,
    where 5- or 6-membered heterocyclyl for its part may be substituted by a substituent selected from the group consisting of oxo and methyl,
  and
  where $(C_4-C_6)$-cycloalkyl and 5- or 6-membered heterocyclyl may be substituted by 1 or 2 substituents independently of one another selected from the group consisting of methyl, hydroxyl, methoxy, hydroxycarbonyl, methoxycarbonyl, ethoxycarbonyl, amino, methylamino and N,N-dimethylamino, and salts, solvates and solvates of the salts thereof.

In the context of the present invention, preference is also given to compounds of the formula (I) in which X represents O or S, $R^1$ represents phenyl, thiazolyl, oxazolyl or pyridyl,
  where phenyl and pyridyl are substituted by 1 or 2 substituents independently of one another selected from the group consisting of fluorine, chlorine, cyano, methyl, trifluoromethyl, methoxy, hydroxycarbonyl, methoxycarbonyl, ethoxycarbonyl, aminocarbonyl, methylaminocarbonyl, ethylaminocarbonyl, N,N-dimethylaminocarbonyl and N,N-diethylaminocarbonyl,
  and
  where thiazolyl and oxazolyl are substituted by a -L-$R^5$ substituent,
    in which
    L represents a bond or NH,
    $R^5$ represents phenyl,
      where phenyl for its part may be substituted by 1 or 2 substituents independently of one another selected from the group consisting of fluorine, chlorine, methyl, methoxy, ethoxy, hydroxycarbonyl, methoxycarbonyl and ethoxycarbonyl,
  and
  where thiazolyl and oxazolyl may be substituted by substituents selected from the group consisting of fluorine, methyl, ethyl, methoxy, hydroxycarbonyl and methoxycarbonyl, $R^2$ represents hydrogen or methyl, $R^3$ represents phenyl, pyrrolyl, oxazolyl, thiazolyl, isoxazolyl, pyrazolyl, imidazolyl and pyridyl,
  where phenyl, pyrrolyl, oxazolyl, thiazolyl, isoxazolyl, pyrazolyl, imidazolyl and pyridyl may be substituted by 1 or 2 substituents independently of one another selected from the group consisting of fluorine, $(C_1-C_6)$-alkyl, hydroxyl, $(C_1-C_4)$-alkoxy and —$NR^AR^B$,
    where $(C_1-C_6)$-alkyl and $(C_1-C_4)$-alkoxy may be substituted by 1 to 3 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino,
    and
    in which
    $R^A$ represents hydrogen or $(C_1-C_4)$-alkyl,
      where $(C_1-C_4)$-alkyl for its part may be substituted by a substituent selected from the group consisting of hydroxyl and $(C_1-C_4)$-alkoxy,
    $R^B$ represents hydrogen or $(C_1-C_4)$-alkyl,
      where $(C_1-C_4)$-alkyl for its part may be substituted by 1 or 2 substituents independently of one another selected from the group consisting of hydroxyl, $(C_1-C_4)$-alkoxy and hydroxycarbonyl, $R^4$ represents $(C_1-C_6)$-alkyl or $(C_4-C_6)$-cycloalkyl,
  where $(C_1-C_6)$-alkyl may be substituted by 1 or 2 substituents independently of one another selected from the group consisting of fluorine, trifluoromethyl, $(C_3-C_7)$-cycloalkyl, hydroxyl, methoxy and ethoxy,
  and
  where $(C_4-C_6)$-cycloalkyl may be substituted by 1 or 2 substituents independently of one another selected from the group consisting of methyl, hydroxyl and methoxy,
and salts, solvates and solvates of the salts thereof.

In the context of the present invention, particular preference is given to compounds of the formula (I) in which
X represents S,
$R^1$ represents phenyl, thiazolyl, oxazolyl or pyridyl,
  where phenyl and pyridyl are substituted by 1 or 2 substituents independently of one another selected from the group consisting of fluorine, chlorine, cyano, methyl, trifluoromethyl, methoxy, hydroxycarbonyl, methoxycarbonyl, ethoxycarbonyl, aminocarbonyl, methylaminocarbonyl, ethylaminocarbonyl, N,N-dimethylaminocarbonyl and N,N-diethylaminocarbonyl,
  and
  where thiazolyl and oxazolyl are substituted by a -L-$R^5$ substituent,
    in which
    L represents a bond or NH,
    $R^5$ represents phenyl,
      where phenyl for its part may be substituted by 1 or 2 substituents independently of one another selected from the group consisting of fluorine, chlorine, methyl, methoxy, ethoxy, hydroxycarbonyl, methoxycarbonyl and ethoxycarbonyl,
    and
    where thiazolyl and oxazolyl may be substituted by a substituent selected from the group consisting of fluorine, methyl, ethyl, methoxy, hydroxycarbonyl and methoxycarbonyl,
$R^2$ represents hydrogen,
$R^3$ represents phenyl or thiazolyl,
  where phenyl may be substituted by 1 or 2 substituents independently of one another selected from the group consisting of $(C_1-C_6)$-alkyl, hydroxyl and $(C_1-C_4)$-alkoxy,
    where $(C_1-C_6)$-alkyl and $(C_2-C_4)$-alkoxy may be substituted by 1 or 2 substituents independently of one another selected from the group consisting of hydroxyl and methoxy,
  and
  where thiazolyl may be substituted by a $(C_1-C_6)$-alkyl substituent,
    where $(C_1-C_6)$-alkyl may be substituted by 1 or 2 substituents independently of one another selected from the group consisting of hydroxyl and methoxy,
$R^4$ represents $(C_1-C_4)$-alkyl,
  where alkyl may be substituted by 1 or 2 hydroxyl substituents,
and salts, solvates and solvates of the salts thereof.

In the context of the present invention, preference is also given to compounds of the formula (I) in which
$R^1$ represents phenyl or pyridyl,
  where phenyl and pyridyl are substituted by 1 or 2 substituents independently of one another selected from the group consisting of fluorine, chlorine, cyano, methyl, trifluoromethyl, methoxy, hydroxycarbonyl, methoxycarbonyl, ethoxycarbonyl, aminocarbonyl, methylaminocarbonyl, ethylaminocarbonyl, cyclopropylaminocarbonyl, N,N-dimethylaminocarbonyl and N,N-diethylaminocarbonyl.

In the context of the present invention, preference is also given to compounds of the formula (I) in which
$R^1$ represents thiazolyl or oxazolyl,
  where thiazolyl and oxazolyl are substituted by a -L-$R^5$ substituent,
    in which
    L represents a bond or NH,
    $R^5$ represents phenyl,
      where phenyl for its part may be substituted by 1 or 2 substituents independently of one another selected from the group consisting of fluorine, chlorine, methyl, methoxy, ethoxy, hydroxycarbonyl, methoxycarbonyl and ethoxycarbonyl,
    and
    where thiazolyl and oxazolyl may be substituted by substituents selected from the group consisting of fluorine, methyl, methoxy, hydroxycarbonyl and methoxycarbonyl.

In the context of the present invention, preference is also given to compounds of the formula (I) in which
$R^3$ represents phenyl,
  where phenyl may be substituted by 1 or 2 substituents independently of one another selected from the group consisting of hydroxyl, $(C_1-C_6)$-alkyl and $(C_1-C_4)$-alkoxy,
    where $(C_1-C_6)$-alkyl and $(C_2-C_4)$-alkoxy may be substituted by 1 or 2 substituents independently of one another selected from the group consisting of hydroxyl and methoxy.

In the context of the present invention, preference is also given to compounds of the formula (I) in which
$R^4$ represents $(C_1-C_6)$-alkyl, $(C_4-C_6)$-cycloalkyl or 5- or 6-membered heterocyclyl,
  where $(C_1-C_6)$-alkyl may be substituted by 1 or 2 substituents independently of one another selected from the group consisting of fluorine, trifluoromethyl, $(C_3-C_7)$-cycloalkyl, hydroxyl, methoxy, ethoxy, hydroxycarbonyl, methoxycarbonyl, ethoxycarbonyl, amino, methylamino, ethylamino, N,N-dimethylamino, N,N-diethylamino and 5- or 6-membered heterocyclyl,
    where ethoxy for its part may be substituted by a substituent selected from the group consisting of hydroxyl and methoxy,
  and
  where $(C_3-C_7)$-cycloalkyl and 5- or 6-membered heterocyclyl may be substituted by 1 or 2 substituents independently of one another selected from the group consisting of methyl, hydroxyl, methoxy, hydroxycarbonyl, methoxycarbonyl, ethoxycarbonyl, amino, methylamino and N,N-dimethylamino.

In the context of the present invention, preference is also given to compounds of the formula (I) in which X represents O or S.

In the context of the present invention, preference is also given to compounds of the formula (I) in which X represents S.

In the context of the present invention, preference is also given to compounds of the formula (I) in which X represents O.

In the context of the present invention, preference is also given to compounds of the formula (I) in which $R^2$ represents hydrogen.

In the context of the present invention, preference is also given to compounds of the formula (I) in which $R^2$ represents methyl.

In the context of the present invention, preference is also given to compounds of the formula (I) in which
$R^4$ represents $(C_1$-$C_4)$-alkyl,
where alkyl may be substituted by 1 or 2 hydroxyl substituents.

The present invention furthermore provides a process for preparing the compounds of the formula (I) according to the invention, characterized in that

[A] a compound of the formula (II-A)

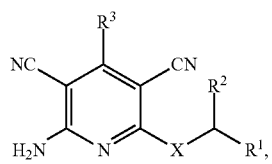
(II-A)

in which X, $R^1$, $R^2$ and $R^3$ each have the meanings given above, is initially, using copper(II) chloride and isoamyl nitrite in a suitable solvent, converted into a compound of the formula (III-A)

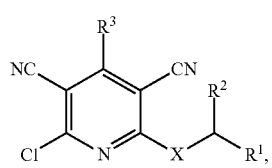
(III-A)

in which X, $R^1$, $R^2$ and $R^3$ each have the meanings given above, and this is then reacted in an inert solvent in the presence of a suitable base with a compound of the formula (IV)

$R^4$—OH        (IV), in which $R^4$ has the meaning given above, oder

[B] in the case that X represents S, a compound of the formula (II-B)

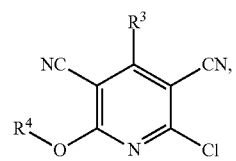
(II-B)

in which $R^3$ and $R^4$ each have the meanings given above, is reacted in an inert solvent with an alkali metal sulphide to give a compound of the formula (III-B)

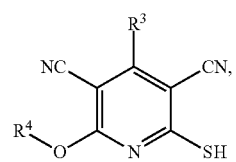
(III-B)

in which $R^3$ and $R^4$ each have the meanings given above, and this is then reacted in an inert solvent in the presence of a base with a compound of the formula (V)

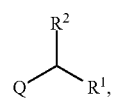
(V)

in which $R^1$ and $R^2$ have the meanings given above and
Q represents a suitable leaving group, preferably halogen, in particular chlorine, bromine or iodine, or represents mesylate, tosylate or triflate,
any protective groups present are then removed and the resulting compounds of the formula (I) are, if appropriate, converted with the appropriate (i) solvents and/or (ii) bases or acids into their solvates, salts and/or solvates of the salts.

In this process, any functional groups present in the compounds of the formulae (II-A) and (II-B) or in the radicals $R^3$ and/or $R^4$—such as, in particular, amino, hydroxyl and carboxyl groups—can, if expedient or required, also be present in temporarily protected form. The introduction and removal of such protective groups takes place in this connection by conventional methods known to the person skilled in the art [see, for example, T. W. Greene and P. G. M. Wuts, *Protective Groups in Organic Synthesis*, Wiley, New York, 1999; M. Bodanszky and A. Bodanszky, *The Practice of Peptide Synthesis*, Springer-Verlag, Berlin, 1984]. If a plurality of protective groups is present, the removal may, if appropriate, take place simulataneously in a one-pot reaction or in separate reaction steps.

The amino protective group which is preferably used is tert-butoxycarbonyl (Boc) or benzyloxycarbonyl (Z). Suitable for protecting carboxyl groups are in particular the appropriate methyl, ethyl or tert-butyl esters. A preferred protective group used for a hydroxyl function is benzyl or a silyl group such as trimethylsilyl, tert-butyldimethylsilyl or dimethylphenylsilyl. If a 1,2- or 1,3-diol grouping is present, preference is given to using a ketal derived from symmetric ketones such as acetone or cyclohexanone (1,3-dioxolane or 1,3-dioxane) as joint protective group.

The process described above can be illustrated in an exemplary manner by Reaction Schemes 1 and 2 below:

Scheme 1
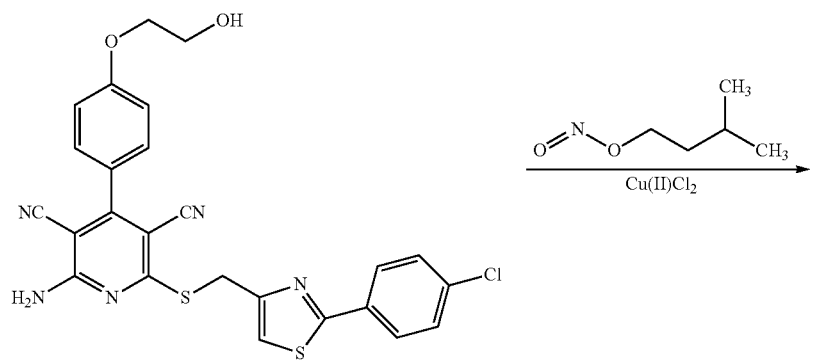
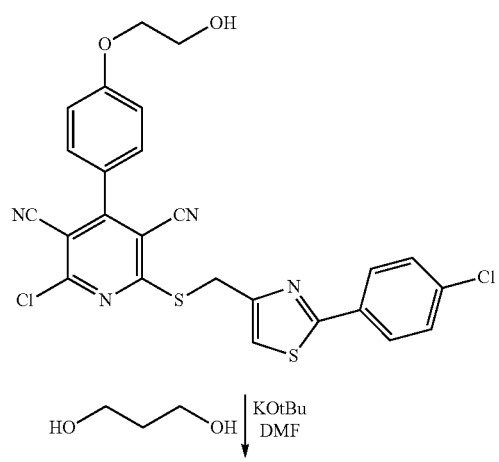
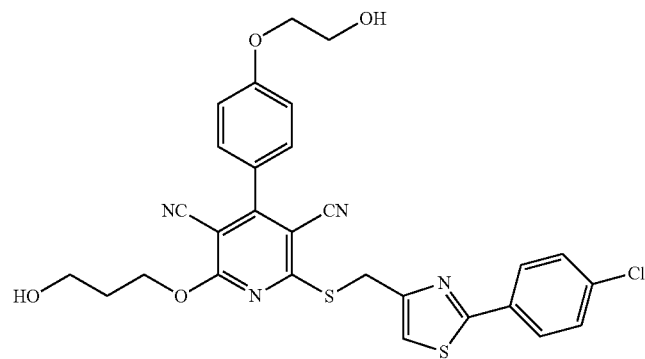

Scheme 2

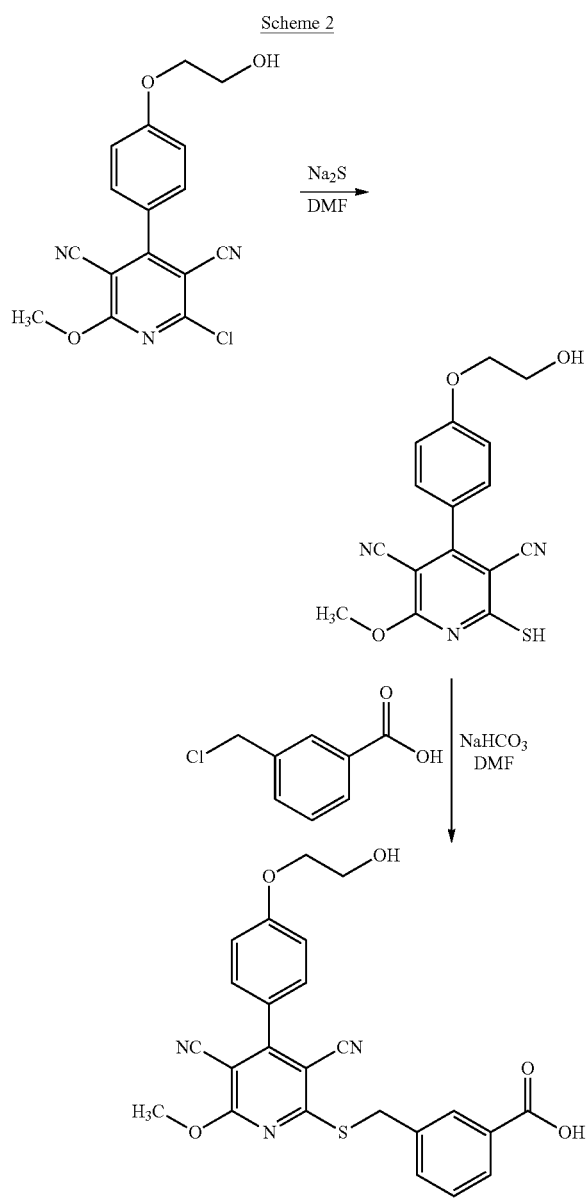

Suitable solvents for the reaction (III-A)+(IV) are all organic solvents which are inert under the reaction conditions. These include ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulphoxide (DMSO), N-methylpyrrolidinone (NMP), acetonitrile or pyridine. It is also possible to use mixtures of the solvents mentioned above. Preference is given to using dimethylformamide.

Suitable bases for this reaction are the customary inorganic or organic bases. These preferably include alkali metal hydrides, such as sodium hydride, alkali metal hydroxides, such as, for example, lithium hydroxide, sodium hydroxide or potassium hydroxide, alkali metal carbonates, such as lithium carbonate, sodium carbonate, potassium carbonate or caesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl) amide, sodium bis(trimethylsilyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN) and also phosphazene bases ("Schwesinger bases"), such as, for example, P2-t-Bu or P4-t-Bu. Preference is given to caesium carbonate, potassium tert-butoxide, sodium hydride and P4-tBu.

Here, the base can be employed in an amount of from 1 to 10 mol, preferably from 1 to 5 mol, in particular from 1 to 3 mol, based on 1 mol of the compound of the formula (IV).

The reaction (III-A)+(IV) is generally carried out in a temperature range of from −78° C. to +140° C., preferably in the range from −20° C. to +100° C., in particular at from 0° C. to +60° C., if appropriate in a microwave oven. The reaction can be carried out at atmospheric, elevated or reduced pressure (for example in the range from 0.5 to 5 bar). The reaction is generally carried out at atmospheric pressure.

The process step (II-A)→(III-A) is generally carried out in a molar ratio of from 2 to 12 mol of copper(II) chloride and 2 to 12 mol of isoamyl nitrite per mole of the compound of the formula (II-A).

Suitable solvents for this process step are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned above. Preferred solvents are acetonitrile and dimethylformamide.

The reaction is generally carried out in a temperature range of from −78° C. to +180° C., preferably in the range from +20° C. to +100° C., in particular at from +20° C. to +60° C., if appropriate in a microwave oven. The reaction can be carried out at atmospheric, elevated or reduced pressure (for example in the range from 0.5 to 5 bar). The reaction is generally carried out at atmospheric pressure.

Suitable solvents for the reaction (III-B)+(V) are all organic solvents which are inert under the reaction conditions. These include ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethylformamide (DMF), dimethyl sulphoxide (DMSO), N-methylpyrrolidinone (NMP), acetonitrile or pyridine. It is also possible to use mixtures of the solvents mentioned above. Preference is given to using dimethylformamide.

Suitable bases for this reaction are the customary inorganic or organic bases. These preferably include alkali metal hydrides, such as sodium hydride, alkali metal hydroxides, such as lithium hydroxide, sodium hydroxide or potassium hydroxide, alkali metal carbonates, such as lithium carbonate, sodium carbonate, potassium carbonate or caesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis(trimethylsilyl)amide, sodium bis(trimethyl-silyl)amide or potassium bis(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]-non-5-ene (DBN). Preference is given to using sodium bicarbonate.

Here, the base is generally employed in an amount of from 1 to 1.25 mol, preferably in an equimolar amount, based on 1 mol of the compound of the formula (V).

The reaction (III-B)+(V) is generally carried out in a temperature range of from −20° C. to +120° C., preferably at from +20° C. to +100° C., if appropriate in a microwave oven. The reaction can be carried out at atmospheric, elevated or reduced pressure (for example in the range from 0.5 to 5 bar). The reaction is generally carried out at atmospheric pressure.

In the reaction (II-B)→(III-B), the alkali metal sulphide used is preferably sodium sulphide in an amount of from 1 to 10 mol, preferably from 1 to 8 mol, in particular from 1 to 5 mol, per mole of the compound of the formula (II-B).

Suitable solvents for this process step are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or dipolar solvents, such as acetonitrile, pyridine, dimethylformamide, dimethyl sulphoxide or N-methylpyrrolidinone.

Another suitable solvent is water. It is also possible to use mixtures of the solvents mentioned above. The preferred solvent is dimethylformamide.

The reaction is generally carried out in a temperature range of from 0° C. to +180° C., preferably in the range from +20° C. to +120° C., in particular at from +40° C. to +100° C., if appropriate in a microwave oven. The reaction can be carried out at atmospheric, elevated or reduced pressure (for example in the range from 0.5 to 5 bar). The reaction is generally carried out at atmospheric pressure.

Alternatively, compounds of the formula (I) in which X represents O can be obtained from compounds of the formula (II-B) by reaction with compounds of the formula (VI)

(VI)

in which $R^1$ and $R^2$ have the meanings given above.

Suitable inert solvents for the reaction (II-B)+(VI)→(I) are in particular acyclic and cyclic ethers such as diethyl ether, methyl tert-butyl ether, 1,2-dimethoxyethane, tetrahydrofuran and dioxane, hydrocarbons, such as benzene, toluene, xylene, hexane and cyclohexane, or other solvents, such as dimethylformamide (DMF), dimethyl sulfoxide (DMSO), N-methylpyrrolidinone (NMP) and pyridine. It is also possible to use mixtures of the solvents mentioned above. Preference is given to using dimethylformamide.

Suitable bases for this reaction are in particular alkali metal alkoxides, such as sodium methoxide or potassium methoxide, sodium ethoxide or potassium ethoxide or sodium tert-butoxide or potassium tert-butoxide, alkali metal hydrides, such as lithium hydride, sodium hydride or potassium hydride, amides, such as sodium amide, lithium bis(trimethylsilyl)amide, sodium bis(trimethylsilyl)amide or potassium bis(trimethylsilyl)amide or lithium diisopropylamide, or organometallic compounds, such as butyllithium or phenyllithium. Preference is given to using potassium tert-butoxide.

Here, the base is generally employed in an amount of from 1 to 1.25 mol, preferably in an equimolar amount, based on 1 mol of the compound of the formula (VI).

The reactions (II-B)+(VI)→(I) are generally carried out in a temperature range of from −20° C. to +120° C., preferably at from +20° C. to +100° C., if appropriate in a microwave oven. The reaction can be carried out at atmospheric, elevated or reduced pressure (for example in the range from 0.5 to 5 bar). The reaction is generally carried out at atmospheric pressure.

The compounds of the formulae (IV) and (VI) are commercially available, known from the literature or can be prepared by methods known from the literature.

The compounds of the formula (V) are commercially available, known from the literature or can be prepared by methods known from the literature. Thus, for example, 2-substituted oxazole and thiazole derivatives of the formulae (V-A), (V-B) and (V-C) can be obtained by reaction of amides, thioamides and thiourea derivatives, respectively, with a 1,3-dihaloacetone (see Scheme 3):

Scheme 3

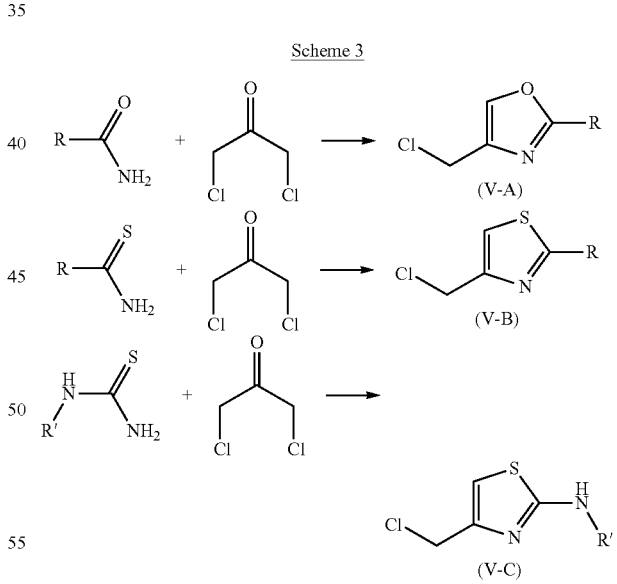

In the case of the compounds (V-C), these can be prepared and isolated either analogously to the literature [cf., for example, I. Simiti et al., Chem. Ber. 95, 2672-2679 (1962)], or they can be generated in situ and directly reacted further. Preferred is the in situ generation using 1,3-dichloroacetone in the solvent dimethylformamide or ethanol. The preparation is generally carried out in a temperature range of from 0° C. to +140° C., preferably in the range from +20° C. to +120° C., in particular at from +60° C. to +100° C.

Compounds of the formula (II-A) where X represents S can be prepared analogously to methods known from the literature, for example by reacting aldehydes of the formula (VII)

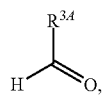

(VII)

in which

R³ᴬ represents phenyl or 5- or 6-membered heteroaryl which is attached via carbon where phenyl and 5- or 6-membered heteroaryl which is attached via carbon may be substituted within the scope of the meaning given above, in the presence of a base with two equivalents of cyanothioacetamide to give compounds of the formula (VIII)

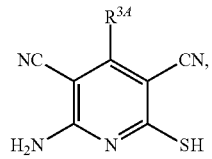

(VIII)

in which R³ᴬ has the meaning given above, and subsequently reacting these in an inert solvent in the presence of a base with a compound of the formula (V) [see Schema 4; cf., for example, Dyachenko et al., *Russ. J. Chem.* 33 (7), 1014-1017 (1997), 34 (4), 557-563 (1998); Dyachenko et al., *Chemistry of Heterocyclic Compounds* 34 (2), 188-194 (1998); Qintela et al., *Eur. J. Med. Chem.* 33, 887-897 (1998); Kandeel et al., *Z. Naturforsch.* 42b, 107-111 (1987); Reddy et al., *J. Med. Chem.* 49, 607-615 (2006); Evdokimov et al., *Org. Lett.* 8, 899-902 (2006)].

Scheme 4

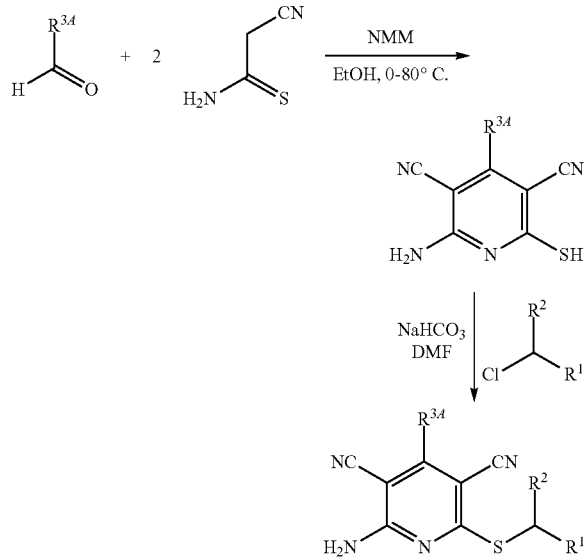

The compounds of the formula (VII) are commercially available, known from the literature or can be prepared by methods known from the literature.

For the reaction (VIII)→(II-A), the conditions mentioned for process step (III-B)+(V)→(I) are used.

Compounds of the formula (II-A) where X represents O can be obtained from compounds of the formula (IX)

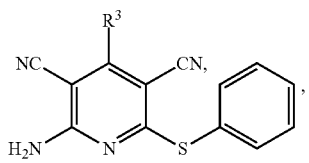

(IX)

in which R³ has the meaning given above, by reaction in an inert solvent in the presence of a suitable base with a compound of the formula (VI).

For this process step, the conditions mentioned for the reaction (II-B)+(VI)→(I) are used.

This preparation method is illustrated by the reaction scheme below:

Scheme 5

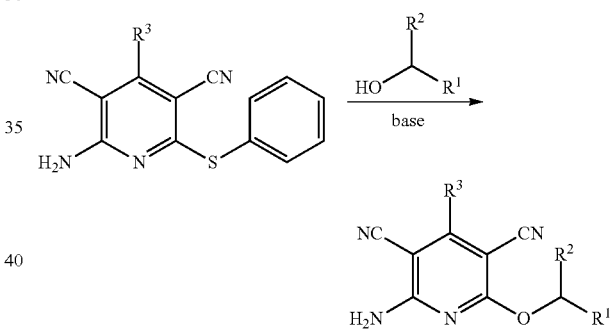

The compounds of the formula (IX) can be prepared analogously to processes described in the literature [cf., for example, Kambe et al., *Synthesis,* 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)] or by reacting compounds of the formula (II) in which X represents S analogously to processes described in the literature [cf., for example, Fujiwara, H. et al., *Heterocycles* 1993, 36 (5), 1105-1113, Su et al., *J. Med Chem.* 1988, 31, 1209-1215].

Compounds of the formula (II-B) can be prepared by converting compounds of the formula (VII) in a suitable solvent in the presence of a suitable base with 2 equivalents of malononitrile and compounds of the formula (X)

R⁴—O⁻M⁺ (X), in which R⁴ has the meaning given above and

M⁺ represents e in alkali metal ion, preferably a sodium or potassium ion, into compounds of the formula (XI)

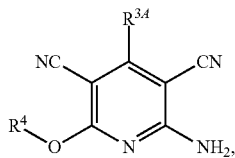

(XI)

in which $R^{3A}$ and $R^4$ each have the meanings given above,
and then reacting these with copper(II) chloride and isoamyl nitrite in a suitable solvent.

The process described is illustrated in an exemplary manner by the reaction scheme below:

Scheme 6

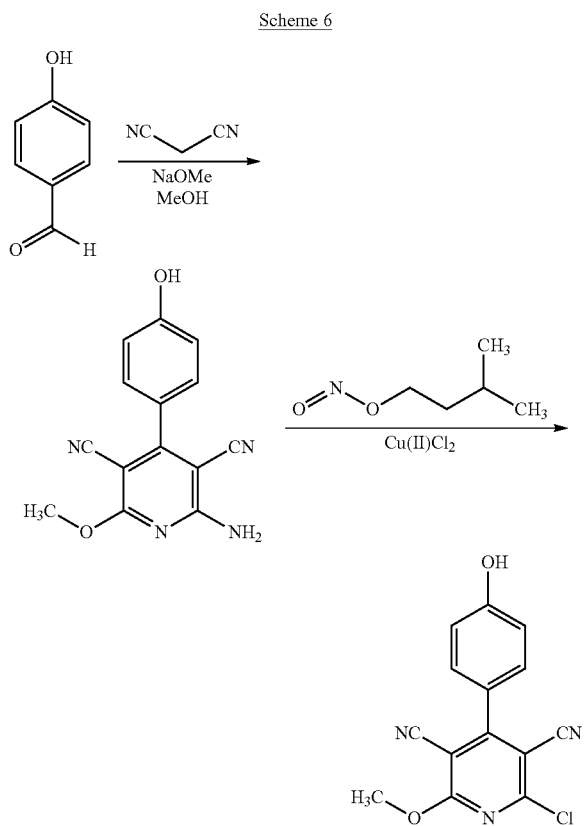

Further compounds of the formula (II-A) in which X represents S can be prepared by converting the compound of the formula (XII)

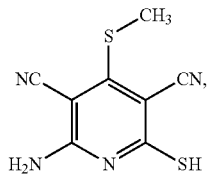

(XII)

in an inert solvent in the presence of a base with a compound of the formula (V) into a compound of the formula (XIII)

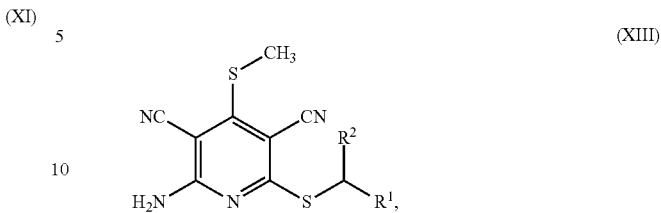

(XIII)

in which $R^1$ and $R^2$ have the meanings given above,
and then reacting this in an inert solvent or in the absence of a solvent with a compound of the formula (XIV)

$$R^{3B}—H \qquad (XIV),$$

in which $R^{3B}$ represents 5- or 6-membered heteroaryl which is attached via nitrogen, where 5- or 6-membered heteroaryl which is attached via nitrogen may be substituted within the scope of the meaning given above for $R^3$.

The reaction (XII)+(V)→(XIII) is carried out under the conditions mentioned for process step (III-B)+(V)→(I).

Suitable solvents for the process step (XIII)+(XIV) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane and chlorobenzene, or other solvents, such as dimethylformamide (DMF), dimethyl sulfoxide (DMSO), N-methylpyrrolidinone (NMP), acetonitrile and pyridine. Another suitable solvent is water. It is also possible to use mixtures of the solvents mentioned above. If appropriate, the reaction can also advantageously be carried out in the presence of an excess of the compound (XIV) without addition of a further solvent. The reaction is preferably carried out in the solvent acetone or N-methylpyrrolidinone.

The process step (XIII)+(XIV) is generally carried out in a temperature range of from 0° C. to +180° C., preferably in the range from +20° C. to +100° C., in particular at from +60° C. to +100° C., if appropriate in a microwave oven. The reaction can be carried out at atmospheric, elevated or reduced pressure (for example in the range from 0.5 to 5 bar). The reaction is generally carried out at atmospheric pressure.

The compounds of the formula (XIV) are commercially available, known from the literature or can be prepared by methods known from the literature.

The compound of the formula (XII) can be obtained in a simple manner by reacting [bis(methyl-thio)methylene]malononitrile with cyanothioacetamide in the presence of a base such as triethylamine.

Further compounds of the formula (II-A) in which X represents O can be prepared by converting the compound of the formula (XV)

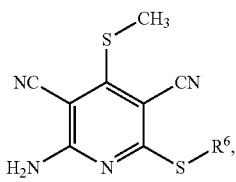

(XV)

in which
R[6] represents $(C_1-C_4)$-alkyl or phenyl,
in an inert solvent in the presence of a base with a compound of the formula (VI) into a compound of the formula (XVI)

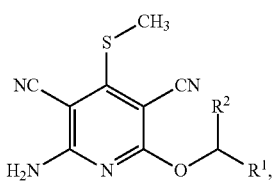

(XVI)

in which R[1] and R[2] have the meanings given above,
and then reacting this in an inert solvent or in the absence of a solvent with a compound of the formula (XIV), or
alternatively reacting a compound of the formula (XV) initially in an inert solvent or in the absence of a solvent with a compound of the formula (XIV) to give compounds of the formula (XVII)

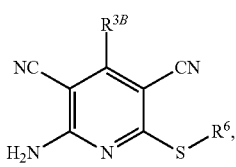

(XVII)

in which R[3B] and R[6] each have the meanings given above,
and then reacting these in an inert solvent in the presence of a suitable base with a compound of the formula (VI).

The compounds of the formula (XV), in which R[6] represents phenyl can be prepared from the compound of the formula (XII) analogously to the process described in Fujiwara, H. et al., *Heterocycles* 1993, 36 (5), 1105-1113.

The compounds of the formula (XV) in which R[6] represents $(C_1-C_4)$-alkyl can be prepared from the compound of the formula (XII) analogously to the process described in Su et al., *J. Med Chem.* 1988, 31, 1209-1215.

The reaction (XV)+(VI) is carried out under the conditions mentioned for process step (II-B)+(VI)→(I).

Suitable solvents for the process steps (XV) and (XVI)+(XIV) are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane and chlorobenzene, or other solvents, such as dimethylformamide (DMF), dimethyl sulphoxide (DMSO), N-methylpyrrolidinone (NMP), acetonitrile and pyridine. Another suitable solvent is water. It is also possible to use mixtures of the solvents mentioned above. If appropriate, the reaction can also advantageously be carried out in the presence of an excess of the compound (XIV) without addition of a further solvent. The reaction is preferably carried out in the solvent acetone or N-methylpyrrolidinone.

The process step (XV) or (XVI)+(XIV) is generally carried out in a temperature range of from 0° C. to +180° C., preferably in the range from +20° C. to +100° C., in particular at from +60° C. to +100° C., if appropriate in a microwave oven. The reaction can be carried out at atmospheric, elevated or reduced pressure (for example in the range from 0.5 to 5 bar). The reaction is generally carried out at atmospheric pressure.

The processes described above are illustrated in the schemes below:

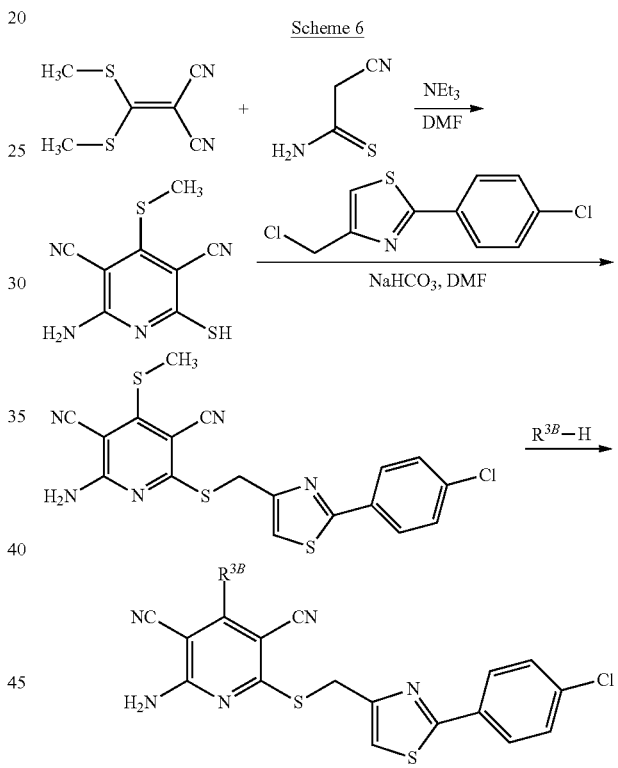

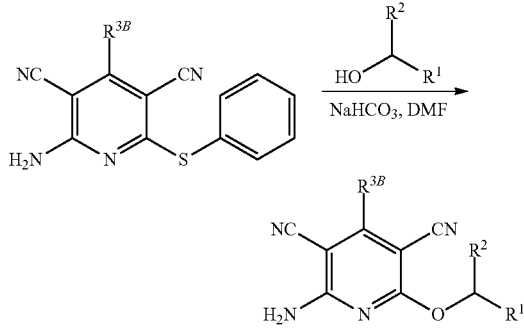

Other compounds according to the invention can, if appropriate, also be prepared by converting functional groups of individual substituents, in particular those listed under $R^1$, $R^2$, $R^3$, $R^4$ and $R^5$, starting with the compounds of the formula (I) obtained by the above processes. These conversions are carried out by customary methods known to the person skilled in the art and include, for example, reactions such as nucleophilic and electrophilic substitutions, oxidations, reductions, hydrogenations, transition metal-catalyzed coupling reactions, eliminations, alkylation, amination, esterification, ester cleavage, etherification, ether cleavage, formation of carboxamides, and also the introduction and removal of temporary protective groups.

Compared to the substances known from the prior art, the compounds according to the invention have an improved property profile, such as, for example, increased solubility in aqueous-organic solvent systems which are relevant for the formulation, a longer pharmacokinetic half-life after oral administration and/or increased metabolic stability.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

Surprisingly, the compounds according to the invention have an unforeseeable useful pharmacological activity spectrum and are therefore particularly suitable for the prophylaxis and/or treatment of disorders.

The pharmaceutical activity of the compounds according to the invention can be explained by their action as potent, selective ligands at adenosine A1 and/or A2b receptors. Here, they act as selective A1 agonists, as selective dual A1/A2b agonists or as selective A1 antagonists. The compounds according to the invention have an identical or improved physicochemical, pharmacokinetic and/or therapeutic profile. The compounds according to the invention act mainly as selective adenosine A1 agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in sections B-1 and B-5.

Depending on their particular structure, the compounds according to the invention can act as full or as partial adenosine receptor agonists or as adenosine receptor antagonists. Partial adenosine receptor agonists are defined here as receptor ligands which trigger a functional response at adenosine receptors which is less than that of full agonists (such as, for example, adenosine itself). Accordingly, partial agonists have lower activity with respect to receptor activation than full agonists.

The compounds of the formula (I) are suitable alone or in combination with one or more other active ingredients for the prophylaxis and/or treatment of various disorders, for example disorders of the cardiovascular system (cardiovascular disorders), for cardio protection following lesions of the heart, and of metabolic disorders and kidney disorders.

Disorders of the cardiovascular system, or cardiovascular disorders, mean in the context of the present invention for example the following disorders: hypertension, peripheral and cardiac vascular disorders, coronary heart disease, coronary restenosis such as, for example, restenosis following balloon dilatation of peripheral blood vessels, myocardial infarction, acute coronary syndrome, acute coronary syndrome with ST elevation, acute coronary syndrome without ST elevation, stable and unstable angina pectoris, myocardial insufficiency, princemetal angina, persistent ischemic dysfunction ("hibernating myocardium"), temporary postischemic dysfunction ("stunned myocardium"), heart failure, tachycardia, atrial tachycardia, arrhythmias, atrial and ventricular fibrillation, persistent atrial fibrillation, permanent atrial fibrillation, atrial fibrillation with normal left ventricular function, atrial fibrillation with impaired left ventricular function, Wolff-Parkinson-White syndrome, disturbances of peripheral blood flow, elevated levels of fibrinogen and of low density LDL, and elevated concentrations of plasminogen activator inhibitor 1 (PAI-1), especially coronary heart disease, acute coronary syndrome, angina pectoris, heart failure, myocardial infarction and atrial fibrillation.

In the context of the present invention, the term heart failure includes both acute and chronic manifestations of heart failure, as well as more specific or related types of disease, such as acute decompensated heart failure, right heart failure, left heart failure, global failure, ischemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are further also suitable for reducing the area of myocardium affected by an infarction, and for the prophylaxis of secondary infarctions.

The compounds according to the invention are furthermore suitable for the prophylaxis and/or treatment of thromboembolic disorders, reperfusion damage following ischemia, micro- and macrovascular lesions (vasculitis), arterial and venous thromboses, edemas, ischemias such as myocardial infarction, stroke and transient ischemic attacks, for cardio protection in connection with coronary artery bypass operations (CABG), primary PTCAs, PTCAs after thrombolysis, rescue PTCA, heart transplants and open-heart operations, and for organ protection in connection with transplants, bypass operations, catheter examinations and other surgical procedures.

Furthermore, the compounds according to the invention are suitable for the treatment and/or prevention of kidney diseases, in particular of renal insufficiency. In the context of the present invention, the term renal insufficiency comprises both acute and chronic manifestations of renal insufficiency, as well as underlying or related kidney diseases such as renal hypoperfusion, obstructive uropathy, glomerulonephritis, acute glomerulonephritis, tubulointerstitial diseases, nephropathic diseases such as primary and congenital kidney disease, nephritis, nephropathy induced by toxic substances, diabetic nephropathy, pyelonephritis, renal cysts and nephrosclerosis, which can be characterized diagnostically for example by abnormally reduced creatinine and/or water excretion, abnormally raised blood concentrations of urea, nitrogen, potassium and/or creatinine, altered activity of renal enzymes, such as, for example, glutamylsynthetase, altered urine osmolarity or urine volume, increased microalbuminuria, macroalbuminuria, lesions on glomeruli and arterioles, tubular dilatation, hyperphosphatemia and/or need for dialysis. The present invention also comprises the use of the compounds according to the invention for the treatment and/or prevention of sequelae of renal insufficiency, for example pulmonary edema, heart failure, uraemia, anemia, electrolyte disturbances (for example hyperkalemia, hyponatremia) and disturbances in bone and carbohydrate metabolism.

Other areas of indication for which the compounds according to the invention can be employed are, for example, the prevention and/or treatment of disorders of the urogenital tract, such as, for example, irritable bladder, erectile dysfunction and female sexual dysfunction, but in addition also the prevention and/or treatment of inflammatory disorders, such as, for example, inflammatory dermatoses (psoriasis, acne, eczema, neurodermitis, dermatitis, keratitis, formation of scars, formation of warts, frostbites), of disorders of the central nervous system and neurodegenerative disorders (strokes, Alzheimer's disease, Parkinson's disease, dementia, epilepsy, depression, multiple sclerosis), of states of pain, cancerous diseases (skin cancer, liposarcomas, carcinomas of the gastrointestinal tract, the liver, pancreas, lung, kidney, ureter, prostate and the genital tract), and also of nausea and emesis associated with cancer therapies.

Other areas of indication are, for example, the prevention and/or treatment of inflammatory and immune disorders (Crohn's disease, ulcerative colitis, lupus erythematodes, rheumatoid arthritis) and respiratory disorders, such as, for example, chronic obstructive pulmonary disease (chronic bronchitis, COPD), asthma, pulmonary emphysema, bronchiectases, cystic fibrosis (mucoviscidosis) and pulmonary hypertension, in particular pulmonary arterial hypertension.

Finally, the compounds according to the invention are also suitable for the prevention and/or treatment of diabetes, in particular diabetes mellitus, gestation diabetes, insulin-dependent diabetes and non-insulin-dependent diabetes, of diabetic sequelae such as, for example, retinopathy, nephropathy and neuropathy, of metabolic disorders (metabolic syndrome, hyperglycemia, gestational diabetes, hyperinsulinemia, insulin resistance, glucose intolerance, obesity (adipositase)) and also of arteriosclerosis and dyslipidemias (hypercholesterolemia, hypertriglyceridemia, elevated concentrations of postprandial plasma triglycerides, hypoalphalipoproteinemia, combined hyperlipidemias), in particular of diabetes, metabolic syndrome and dyslipidemias.

In addition, the compounds according to the invention can also be used for the treatment and/or prevention of disorders of the thyroid gland (hyperthyreosis), disorders of the pancreas (pancreatitis), fibrosis of the liver, viral diseases (HPV, HCMV, HIV), cachexia, osteoporosis, gout, incontinence, and also for wound healing and angiogenesis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The present invention furthermore provides the compounds according to the invention for use in a method for the treatment and/or prophylaxis of coronary heart disease, acute coronary syndrome, angina pectoris, heart failure, myocardial infarction and atrial fibrillation.

The present invention furthermore provides the compounds according to the invention for methods for the treatment and/or prophylaxis of diabetes, metabolic syndrome and dyslipidemias.

The compounds according to the invention can be used alone or, if required, in combination with other active ingredients. The present invention furthermore provides medicaments comprising at least one of the compounds according to the invention and one or more further active ingredients, in particular for the treatment and/or prevention of the disorders mentioned above.

Suitable active ingredients for combination are, by way of example and by way of preference: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, antidepressants and other psychopharmaceuticals.

The present invention relates in particular to combinations of at least one of the compounds according to the invention with at least one lipid metabolism-altering active ingredient, antidiabetic, blood pressure-reducing active ingredient and/or agent having antithrombotic effects.

The compounds according to the invention can preferably be combined with one or more lipid metabolism-modulating active ingredients, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulphonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active ingredients, by way of example and by way of preference from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example and by way of preference from the group of the platelet aggregation inhibitors or the anticoagulants;

diuretics;

vasopressin receptor antagonists;

organic nitrates and NO donors;

compounds with positive inotropic activity;

compounds which inhibit the degradation of cyclic guanosine monophosphate (cGMP) and/or cyclic adenosine monophosphate (cAMP), such as, for example, inhibitors of phospho-diesterases (PDE) 1, 2, 3, 4 and/or 5, in particular PDE 5 inhibitors, such as sildenafil, vardenafil and tadalafil, and also PDE 3 inhibitors, such as milrinone;

natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin;

agonists of the prostacyclin receptor (IP receptor), such as, by way of example, iloprost, beraprost, cicaprost;

inhibitors of the $I_f$ (funny channel) channel, such as, by way of example, ivabradine;

calcium sensitizers, such as, by way of example and by way of preference, levosimendan;

potassium supplements;

NO-independent, and heme-independent activators of guanylate cyclase, such as, in particular, cinaciguate and the compounds described in WO 01/19355, WO 01/19776, WO 01/19778, WO 01/19780, WO 02/070462 and WO 02/070510;

NO-independent but heme-dependent stimulators of guanylate cyclase, such as, in particular, riociguate and the compounds described in WO 00/06568, WO 00/06569, WO 02/42301 and WO 03/095451;

inhibitors of human neutrophil elastase (HNE), such as, for example, sivelestat and DX-890 (Reltran);

compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, eto-moxir, dichloroacetate, ranolazine and trimetazidine.

Lipid metabolism-modifying active ingredients are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists, PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, dalcetrapib, BAY 60-5521, anacetrapib or CETP vaccine (CETi-1).

In a preferred embodiment of the invention, the compounds according to the invention are administered in combination with a PPAR-γ agonist for example from the class of the thiazolidinediones, such as, by way of example and by way of preference, pioglitazone or rosiglitazone.

In a preferred embodiment of the invention, the compounds according to the invention are administered in combination with a PPAR-δ agonist such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active ingredients. Here, insulin and insulin derivatives include both insulins of animal, human or biotechnological origin and also mixtures thereof. The orally effective hypoglycemic active ingredients preferably include sulphonylureas, biguanides, meglitinide derivatives, glucosidase inhibitors and PPAR-gamma agonists.

In a preferred embodiment of the invention, the compounds according to the invention are administered in combination with insulin.

In a preferred embodiment of the invention, the compounds according to the invention are administered in combination with a sulphonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a DPP-IV inhibitor, such as, by way of example and by way of preference, sitagliptin and vildagliptin.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII antagonist, such as, by way of example and by way of preference, losartan, valsartan, candesartan, embusartan, olmesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinapril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetamide, torsemide, bendroflumethiazide, chlorothiazide, hydrochlorothiazide, hydroflumethiazide, methylclothiazide, polythiazide, trichloromethiazide, chlorthalidone, indapamide, metolazone, quinethazone, acetazolamide, dichlorphenamide, methazolamide, glycerol, isosorbide, mannitol, amiloride or triamteren.

In a preferred embodiment of the invention, the compounds according to the invention are administered in combination with an aldosterone or mineralocorticoid receptor antagonist, such as, by way of example and by way of preference, spironolactone or eplerenone.

In a preferred embodiment of the invention, the compounds according to the invention are administered in combination with a vasopressin receptor antagonist, such as, by way of example and by way of preference, conivaptan, tolvaptan, lixivaptan or SR-121463.

In a preferred embodiment of the invention, the compounds according to the invention are administered in combination with an organic nitrate or NO donor, such as, by way of example and by way of preference, sodium nitroprusside, nitroglycerol, isosorbide mononitrate, isosorbide dinitrate, molsidomine or SIN-1, or in combination with inhalative NO.

In a preferred embodiment of the invention, the compounds according to the invention are administered in combination with a positive-inotropic compound, such as, by way of example and by way of preference, cardiac glycosides (digoxin), beta-adrenergic and dopaminergic agonists, such as isoproterenol, adrenaline, noradrenaline, dopamine or dobutamine.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, dabigatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

In the context of the present invention, particular preference is given to combinations comprising at least one of the compounds according to the invention and also one or more further active ingredients selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

The present invention furthermore provides medicaments comprising at least one compound according to the invention, usually together with one or more inert, nontoxic, pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, otically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert, nontoxic, pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active ingredient, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

Abbreviations Used aq. aqueous
Ex. Example
c concentration
d doublet (in NMR)
dd doublet of doublets (in NMR)
DBU 1,8-diazabicyclo[5.4.0]undec-7-ene
TLC thin-layer chromatography
DCI direct chemical ionization (in MS)
DMF N,N-dimethylformamide
DMSO dimethyl sulphoxide
ee enantiomeric excess
EI electron impact ionization (in MS)
ESI electrospray ionization (in MS)
Et ethyl
m.p. melting point
h hour(s)
HPLC high-pressure, high-performance liquid chromatography
cat. catalytic
conc. concentrated
LC-MS liquid chromatography-coupled mass spectrometry
lit. literature (reference)
Me methyl
MeCN acetonitrile
min minute(s)

MS mass spectrometry
NMM N-methylmorpholine
NMR nuclear magnetic resonance spectrometry
q quartet (in NMR)
rac. racemic
RP-HPLC reversed-phase HPLC
RT room temperature
$R_t$ retention time (in HPLC)
s singlet (in NMR)
s br broad singlet (in NMR)
t triplet (in NMR)
t-Bu tert-butyl
TFA trifluoroacetic acid
THF tetrahydrofuran
dil. dilute HPLC, LC-MS and GC-MS Methods:

Method 1 (LC-MS): MS instrument type: Waters (Micromass) Quattro Micro; HPLC instrument type: Agilent 1100 Series; column: Thermo Hypersil GOLD 3µ 20×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate 2.5 ml)→5.00 min 100% A; oven: 50° C.; flow rate: 2 ml/min; UV detection: 210 nm.

Method 2 (LC-MS): MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 3 (LC-MS): MS instrument type: Micromass ZQ; HPLC instrument type: Waters Alliance 2795; column: Phenomenex Synergi 2.5µ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4 (LC-MS): Instrument: Micromass Quattro Premier with Waters UPLC Acquity; column: Thermo Hypersil GOLD 1.9µ 50×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 5 (LC-MS): MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 6 (LC-MS): MS instrument type: Micromass ZQ; HPLC instrument type: Waters Alliance 2795; column: Merck Chromolith SpeedROD RP-18e 100×4.6 mm; mobile phase A: 1 l of water+0.5 ml of 50% strength formic acid; mobile phase B: 1 l of acetonitrile+0.5 ml of 50% strength formic acid; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 7 (preparative HPLC): column: Grom-Sil C18, 10 µm, 250 mm×30 mm. mobile phase A: water+0.1% formic acid, mobile phase B: acetonitrile. flow rate: 50 ml/min. program: 0-5 min: 10% B; 5-38 min: gradient to 95% B, UV detection: 210 nm.

Method 8 (LC-MS): Instrument: Micromass Quattro LCZ with HPLC Agilent Series 1100; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 9 (LC-MS): Instrument: Micromass Quattro LCZ with HPLC Agilent Series 1100; column: Phenomenex Onyx Monolithic C18, 100 mm×3 mm. mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 10 (LC-MS): MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 11 (LC-MS): MHZ-Q-GEM-1 MS instrument type: Micromass Quattro LCZ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Starting Materials and Intermediates

Example 1A

2-Amino-4-phenyl-6-sulphanylpyridine-3,5-dicarbonitrile

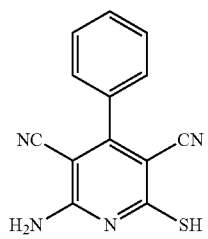 [SMILES: N#Cc1c(N)nc(S)c(C#N)c1-c1ccccc1]

The preparation was carried out as described in WO 03/053441 for Example 6.

MS (ESIpos): m/z=253 [M+H]$^+$

Example 2A

2-Amino-6-({[2-(4-chlorophenyl)-1,3-thiazol-4-yl]methyl}sulphanyl)-4-phenylpyridine-3,5-dicarbonitrile

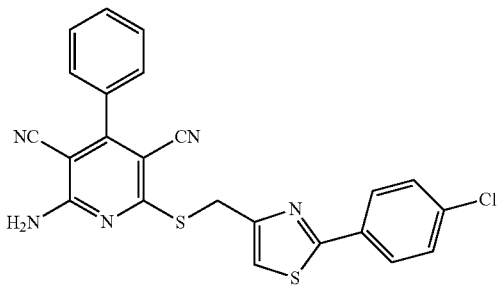 [SMILES: N#Cc1c(N)nc(SCc2csc(-c3ccc(Cl)cc3)n2)c(C#N)c1-c1ccccc1]

2 g (7.927 mmol) of 2-amino-4-phenyl-6-sulphanylpyridine-3,5-dicarbonitrile are initially charged in 15 ml of DMF, 2.13 g (8.720 mmol) of 4-(chloromethyl)-2-(4-chlorophenyl)-1,3-thiazole and 1.99 g (23.781 mmol) of sodium bicarbonate are added and the mixture is stirred at room temperature overnight. Water is added to the reaction mixture, and the precipitated solid is filtered off, washed with MTBE and dried under high vacuum. This gives 3.87 g (100% of theory) of the target compound.

$^1$H-NMR (400 MHz, DMSO-$d_6$): δ=8.14 (s br, 2H), 7.97-7.92 (m, 3H), 7.59-7.50 (m, 7H), 4.64 (s, 2H).

LC-MS (Method 4): $R_t$=1.49 min; MS (ESIpos): m/z=460 [M+H]$^+$.

Example 3A

2-Chloro-6-({[2-(4-chlorophenyl)-1,3-thiazol-4-yl]methyl}sulphanyl)-4-phenylpyridine-3,5-dicarbonitrile

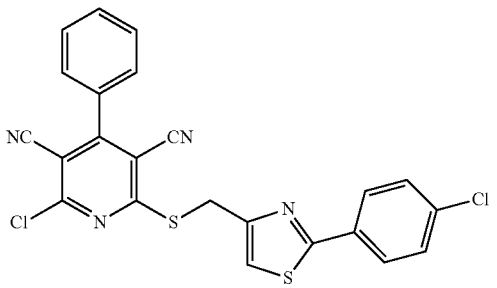 [SMILES: N#Cc1c(Cl)nc(SCc2csc(-c3ccc(Cl)cc3)n2)c(C#N)c1-c1ccccc1]

9 g (19.762 mmol) of 2-amino-6-({[2-(4-chlorophenyl)-1,3-thiazol-4-yl]methyl}sulphanyl)-4-phenylpyridine-3,5-dicarbonitrile are initially charged in 200 ml of acetonitrile, 7.98 ml (59.285 mmol) of isoamyl nitrite and 7.97 g (59.285 mmol) of copper(II) chloride are added and the mixture is stirred at 60° C. for 4 hours. 1N Hydrochloric acid is added to the mixture, and the precipitated solid is filtered off. It is purified on a silica gel column (mobile phase: toluene). This gives 5.98 g (63% of theory) of the target compound.

$^1$H-NMR (400 MHz, DMSO-$d_6$): δ=7.96 (d, 2H), 7.76 (s, 1H), 7.66-7.62 (m, 5H), 7.57 (d, 2H), 4.78 (s, 2H).

LC-MS (Method 3): $R_t$=2.82 min; MS (ESIpos): m/z=479 [M+H]$^+$.

Example 4A

2-Chloro-6-({[2-(4-chlorophenyl)-1,3-thiazol-4-yl]methyl}sulphanyl)-4-[4-(2-hydroxyethoxy)-phenyl]pyridine-3,5-dicarbonitrile

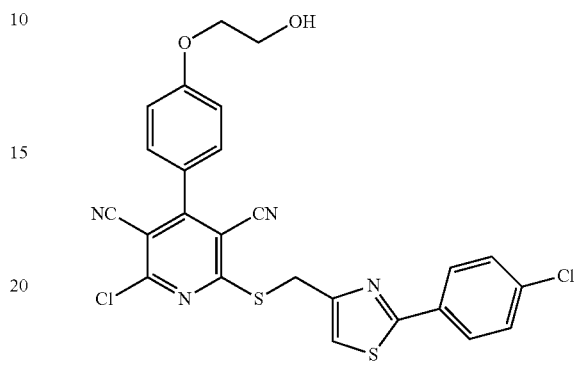

The preparation was carried out analogously to Example 3A from the appropriate starting materials.

LC-MS (Method 2): $R_t$=2.93 min; MS (ESIpos): m/z=539 [M+H]$^+$.

Example 5A

2-Amino-6-sulphanyl-4-(1,3-thiazol-5-yl)pyridine-3,5-dicarbonitrile

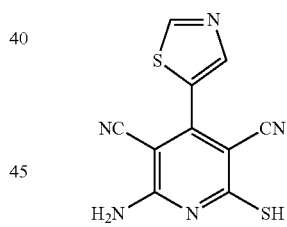

1.14 g (9.539 mmol) of 5-thiazolecarboxaldehyde and 1.91 g (19.077 mmol) of cyanothioacetamide are initially charged in 20 ml of ethanol, 2.097 ml (19.077 mmol) of 4-methylmorpholine are added and the mixture is heated under reflux for 4 hours. The mixture is then stirred at room temperature for 20 hours. The reaction mixture is concentrated and the residue is purified on silica gel (mobile phase: methylene chloride/methanol 100:0→10:1). The product-containing fractions are concentrated and the residue is triturated with acetonitrile. The solid is filtered off and dried under high vacuum. This gives 920 mg (37% of theory) of the target compound.

$^1$H-NMR (400 MHz, DMSO-$d_6$): δ=9.31 (s, 1H), 8.16 (s, 1H), 7.50-6.99 (s br, 2H).

LC-MS (Method 2): $R_t$=1.29 min; MS (ESIpos): m/z=260 [M+H]$^+$.

Example 6A

2-Amino-6-({[2-(4-chlorophenyl)-1,3-thiazol-4-yl]methyl}sulphanyl)-4-(1,3-thiazol-5-yl)pyridine-3,5-dicarbonitrile

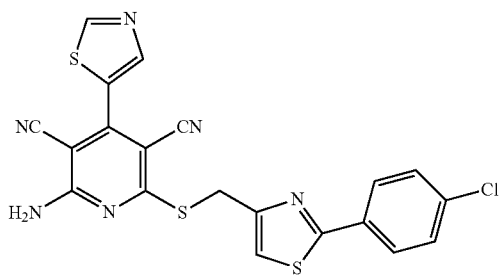 [SMILES: N#Cc1c(N)nc(SCc2csc(-c3ccc(Cl)cc3)n2)c(C#N)c1-c1cncs1]

370 mg (1.427 mmol) of 2-amino-6-sulphanyl-4-(1,3-thiazol-5-yl)pyridine-3,5-dicarbonitrile, 383 mg (1.570 mmol) of 4-(chloromethyl)-2-(4-chlorophenyl)-1,3-thiazole and 359 mg of sodium bicarbonate are stirred in 7 ml of DMF for 1 hour. 150 ml of acetonitrile and 100 ml of water are added to the reaction mixture, and the precipitated solid is filtered off and dried under high vacuum. This gives 569 mg (85% of theory) of the target compound.

$^1$H-NMR (400 MHz, DMSO-$d_6$): δ=9.38 (s, 1H), 8.27 (s, 1H), 8.19-8.03 (s br, 2H), 7.94 (d, 2H), 7.89 (s, 1H), 7.57 (d, 2H), 4.62 (s, 2H).

LC-MS (Method 2): $R_t$=2.67 min; MS (ESIpos): m/z=467 [M+H]$^+$.

Example 7A

2-Chloro-6-({[2-(4-chlorophenyl)-1,3-thiazol-4-yl]methyl}sulphanyl)-4-(1,3-thiazol-5-yl)pyridine-3,5-dicarbonitrile

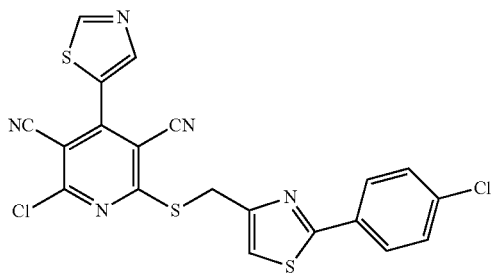 [SMILES: N#Cc1c(Cl)nc(SCc2csc(-c3ccc(Cl)cc3)n2)c(C#N)c1-c1cncs1]

569 mg (1.218 mmol) of 2-amino-6-({[2-(4-chlorophenyl)-1,3-thiazol-4-yl]methyl}sulphanyl)-4-(1,3-thiazol-5-yl)pyridine-3,5-dicarbonitrile are dissolved in 20 ml of concentrated hydrochloric acid, the mixture is cooled to 0° C. and 252 mg (3.655 mmol) of sodium nitrite are added at this temperature. The mixture is stirred at 0° C. for 1 h and then warmed to room temperature and stirred at room temperature overnight. The reaction mixture is purified by preparative HPLC (acetonitrile/water: 10:90→95:5). This gives 445 mg (68% of theory) of the target compound.

$^1$H-NMR (400 MHz, DMSO-$d_6$): δ=9.49 (s, 1H), 8.42 (s, 1H), 7.95 (d, 2H), 7.75 (s, 1H), 7.58 (d, 2H), 4.78 (s, 2H).

LC-MS (Method 2): $R_t$=2.99 min; MS (ESIpos): m/z=486 [M+H]$^+$.

Example 8A

2-Amino-4-[4-(2-hydroxyethoxy)phenyl]-6-methoxypyridine-3,5-dicarbonitrile

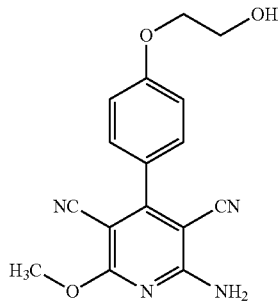 [SMILES: COc1nc(N)c(C#N)c(-c2ccc(OCCO)cc2)c1C#N]

Under argon, 10 g (60.176 mmol) of 4-(2-hydroxyethoxy)benzaldehyde are dissolved in 125 ml of methanol, 8.15 g (123.362 mmol) of malononitrile and 19.506 g (361.058 mmol) of sodium methoxide are added and the mixture is stirred at room temperature for 3 hours. The reaction mixture is then concentrated, and the residue is taken up in ethyl acetate and washed with saturated aqueous ammonium chloride solution. The organic phase is dried over sodium sulphate and concentrated. The residue is triturated with methanol, and the precipitated solid is filtered off and dried under high vacuum. This gives 5.2 g (22% of theory) of the target compound.

$^1$H-NMR (400 MHz, DMSO-$d_6$): δ=8.14-7.80 (s br, 2H), 7.46 (d, 2H), 7.10 (d, 2H), 4.92 (t, 1H), 4.08 (t, 2H), 3.97 (s, 3H), 3.75 (q, 2H).

LC-MS (Method 4): $R_t$=0.86 min; MS (ESIpos): m/z=311 [M+H]$^+$.

Example 9A

2-Chloro-4-[4-(2-hydroxyethoxy)phenyl]-6-methoxypyridine-3,5-dicarbonitrile

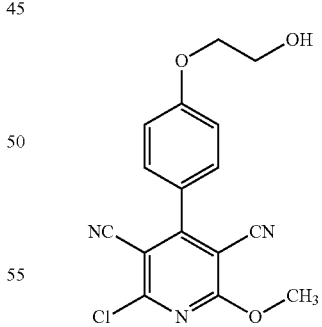

3.3 g (10.634 mmol) of 2-amino-4-[4-(2-hydroxyethoxy)phenyl]-6-methoxypyridine-3,5-dicarbonitrile are initially charged in 300 ml of acetonitrile, 8.578 g (63.806 mmol) of copper(II) chloride and 8.59 ml (63.806 mmol) of isoamyl nitrite are added and the mixture is stirred at room temperature overnight. 1N hydrochloric acid is added, and the reaction mixture is extracted with ethyl acetate. The organic phase is washed with saturated aqueous sodium bicarbonate solution and water, dried over sodium sulphate and concentrated.

Example 10A

4-[4-(2-Hydroxyethoxy)phenyl]-2-methoxy-6-sulphanylpyridine-3,5-dicarbonitrile

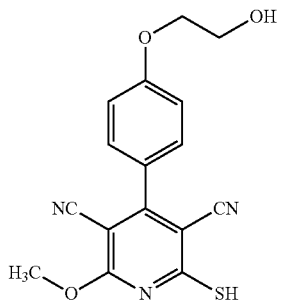 [SMILES: COc1nc(S)c(C#N)c(-c2ccc(OCCO)cc2)c1C#N]

4.0 g (12.1 mmol) of 2-chloro-4-[4-(2-hydroxyethoxy)phenyl]-6-methoxypyridine-3,5-dicarbonitrile are dissolved in 16 ml of anhydrous DMF, 1.42 g (18.2 mmol) of anhydrous sodium sulphide are added and the mixture is stirred at room temperature for 2 h. 36 ml of water are added, and with stirring the solution is slowly added dropwise to a mixture, warmed to 50° C., of 61 ml of 1M hydrochloric acid and 20 ml of methanol. The yellow suspension is stirred at RT for 1 h and filtered off with suction, and the precipitate is washed with water and dried at 45° C. under reduced pressure overnight.

Yield: 3.27 g (82% of theory, purity 29%)

LC-MS (Method 6): $R_t$=3.27 min (29.4 Fl %); MS (ESIpos): m/z=328 [M+H]$^+$

The product is reacted further without further purification. For analytical purposes, a small sample is purified by preparative HPLC (Method 7):

$^1$H-NMR (500 MHz, DMSO-$d_6$): δ=7.59-7.48 (m, 2H), 7.20-7.10 (m, 2H), 4.75-4.35 (br), 4.10 (t, 2H), 3.93 (s, 3H), 3.65 (t, 2H).

Example 11A

2-Mercapto-6-methoxy-4-phenylpyridine-3,5-dicarbonitrile

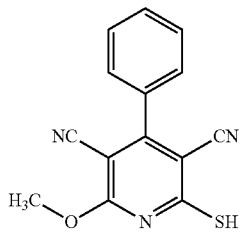 [SMILES: COc1nc(S)c(C#N)c(-c2ccccc2)c1C#N]

The preparation is carried out analogously to Example 10A from the appropriate starting materials.

LC-MS (Method 6): $R_t$=5.72 min; MS (ESIneg): m/z=266 [M−H]$^+$.

Example 12A

2-Amino-6-ethoxy-4-[4-(2-hydroxyethoxy)phenyl]pyridine-3,5-dicarbonitrile

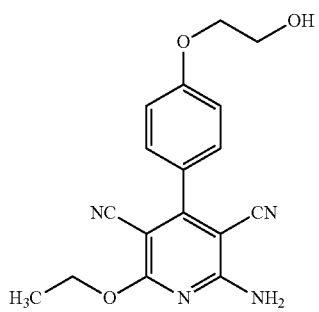 [SMILES: CCOc1nc(N)c(C#N)c(-c2ccc(OCCO)cc2)c1C#N]

40 g (240.705 mmol) of 4-(2-hydroxyethoxy)benzaldehyde are initially charged in 500 ml of ethanol, and 35.6 g (493.445 mmol) of malononitrile are added. 539 ml (1444.232 mmol) of 21% strength sodium methoxide solution in ethanol are then added dropwise. The mixture is stirred at room temperature for 24 hours. The mixture is concentrated, the residue is taken up in ethyl acetate and washed with water and saturated aqueous sodium chloride solution and the organic phase is dried over sodium sulphate and concentrated. The residue is dissolved in ethanol, adsorbed onto silica gel and purified on silica gel (mobile phase: methylene chloride/ethanol 200:1→50:1). The product obtained is suspended in 200 ml of ethanol, 1000 ml of water are added gradually and the mixture is stirred at room temperature for 1 hour. The solid is filtered off, washed with water/ethanol 1:1 and dried at 50° C. in a vacuum drying cabinet. This gives 15.4 g (19% of theory) of the target compound.

$^1$H-NMR (400 MHz, DMSO-$d_6$): δ=8.05-7.72 (s br, 2H), 7.46 (d, 2H), 7.10 (d, 2H), 4.94 (t, 1H), 4.44 (q, 2H), 4.08 (t, 2H), 3.75 (q, 2H), 1.34 (t, 3H).

LC-MS (Method 2): $R_t$=2.02 min; MS (ESIpos): m/z=325 [M+H]$^+$.

Example 13A

2-Chloro-6-ethoxy-4-[4-(2-hydroxyethoxy)phenyl]pyridine-3,5-dicarbonitrile

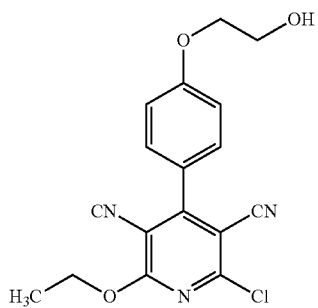

The reaction mixture is purified by preparative HPLC (acetonitrile/water: 10:90→95:5). This gives 2.11 g (58% of theory) of the target compound.

$^1$H-NMR (400 MHz, DMSO-$d_6$): δ=7.60 (d, 2H), 7.19 (d, 2H), 4.13 (s, 3H), 4.11 (t, 2H), 3.75 (t, 2H).

LC-MS (Method 2): $R_t$=2.13 min; MS (ESIpos): m/z=330 [M+H]$^+$.

14.8 g (45.631 mmol) of 2-amino-6-ethoxy-4-[4-(2-hydroxyethoxy)phenyl]pyridine-3,5-dicarbonitrile are initially charged in 830 ml of acetonitrile, 32.07 g (273.785 mmol) of isoamyl nitrite and 36.81 g (273.785 mmol) of copper(II) chloride are added and the mixture is stirred at 60° C. for 3 hours. 800 ml of 1N hydrochloric acid are added, and the reaction mixture is extracted with ethyl acetate. The organic phase is washed with saturated aqueous sodium bicarbonate solution and saturated aqueous sodium chloride solution, dried over sodium sulphate and concentrated. The residue is triturated with ethanol, and the solid is filtered off, washed with ethanol and dried under high vacuum. As the mother liquor still contains product, it is adsorbed onto 35 g of silica gel and purified on a silica gel column (mobile phase: cyclohexane/ethyl acetate 2:1→1:1). This gives a total of 11.9 g (72% of theory) of the target compound.

$^1$H-NMR (400 MHz, DMSO-d$_6$): δ=7.59 (d, 2H), 7.18 (d, 2H), 4.94 (s br, 1H), 4.57 (q, 2H), 4.10 (t, 2H), 3.76 (t, 2H), 1.41 (t, 3H).

LC-MS (Method 8): R$_t$=2.30 min; MS (ESIpos): m/z=344 [M+H]$^+$.

Example 14A

2-Ethoxy-4-[4-(2-hydroxyethoxy)phenyl]-6-sulphanylpyridine-3,5-dicarbonitrile

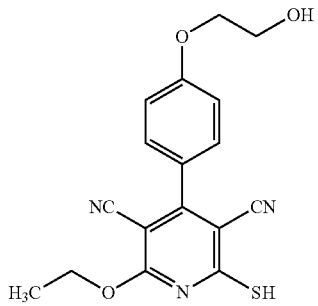 [SMILES: CCOc1nc(S)c(C#N)c(-c2ccc(OCCO)cc2)c1C#N]

1 g (2.909 mmol) of 2-chloro-6-ethoxy-4-[4-(2-hydroxyethoxy)phenyl]pyridine-3,5-dicarbonitrile is initially charged in 7.5 ml of DMF, 454 mg (5.818 mmol) of sodium sulphide are added and the mixture is stirred at room temperature overnight. The mixture is concentrated, the residue is triturated with acetonitrile and the solid is filtered off and dried under high vacuum. This gives 230 mg (24% of theory) of the target compound.

LC-MS (Method 4): R$_t$=0.79 min; MS (ESIpos): m/z=342 [M+H]$^+$.

Example 15A

2-Amino-4-(4-hydroxyphenyl)-6-methoxypyridine-3,5-dicarbonitrile

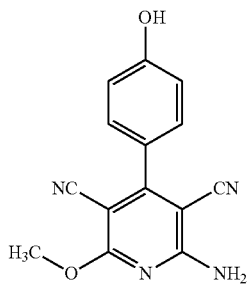 [SMILES: COc1nc(N)c(C#N)c(-c2ccc(O)cc2)c1C#N]

500 mg (4.094 mmol) of 4-hydroxybenzaldehyde and 554 mg (8.393 mmol) of malononitrile are initially charged in 5 ml of methanol, and 4.42 g (24.565 mmol) of sodium methoxide, 30% strength in methanol, are added. The mixture is then stirred at room temperature for 2 hours. The precipitated solid is filtered off, washed with methanol and dried under high vacuum. This gives 613 mg (76% of theory) of the target compound.

LC-MS (Method 3): R$_t$=1.33 min; MS (ESIpos): m/z=267 [M+H]$^+$.

Example 16A

2-Chloro-4-(4-hydroxyphenyl)-6-methoxypyridine-3,5-dicarbonitrile

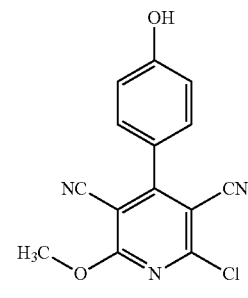 [SMILES: COc1nc(Cl)c(C#N)c(-c2ccc(O)cc2)c1C#N]

7.98 g (15.285 mmol) of 2-amino-4-(4-hydroxyphenyl)-6-methoxypyridine-3,5-dicarbonitrile are initially charged in 120 ml of acetonitrile, 6.175 ml (45.855 mmol) of isoamyl nitrite and 6.165 g (45.855 mmol) of copper(II) chloride are added and the mixture is stirred at room temperature overnight. 1N hydrochloric acid is added, and the reaction mixture is extracted with ethyl acetate. The organic phase is washed with saturated aqueous sodium bicarbonate solution and with water, dried over sodium sulphate and concentrated. The residue is purified on a silica gel column (mobile phase: toluene/ethyl acetate 2:1). This gives 1.3 g (23% of theory) of the target compound.

$^1$H-NMR (400 MHz, DMSO-d$_6$): δ=10.29 (s, 1H), 7.49 (d, 2H), 6.98 (d, 2H), 4.12 (s, 3H).

LC-MS (Method 1): R$_t$=2.04 min; MS (ESIpos): m/z=286 [M+H]$^+$.

Example 17A 4-(4-Hydroxyphenyl)-2-methoxy-6-sulphanylpyridine-3,5-dicarbonitrile

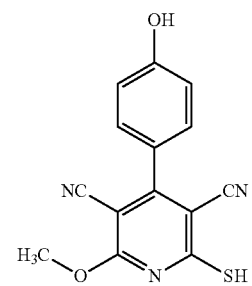 [SMILES: COc1nc(S)c(C#N)c(-c2ccc(O)cc2)c1C#N]

1.3 g (4.550 mmol) of 2-chloro-4-(4-hydroxyphenyl)-6-methoxypyridine-3,5-dicarbonitrile are initially charged in 10 ml of DMF, 426 mg (5.460 mmol) of sodium sulphide are added and the mixture is stirred at room temperature overnight. The reaction mixture is reacted further without any further purification.

LC-MS (Method 4): $R_t$=0.74 min; MS (ESIpos): m/z=284 [M+H]$^+$.

Example 18A 4-(Chloromethyl)-N-(4-fluorophenyl)-1,3-thiazole-2-amine

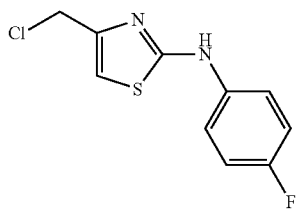 [SMILES: Fc1ccc(Nc2nc(CCl)cs2)cc1]

Method A: Over a period of 1.5 h, a warm solution of 160 g (1.26 mol) of 1,3-dichloroacetone in 480 ml of acetone is metered into a suspension von 202 g (1.19 mol) of 4-fluorophenylthiourea in 660 ml of acetone, and the mixture is stirred at 40° C. for 4.5 h and at RT overnight. The crystals are filtered off with suction, washed with acetone and dried under reduced pressure at 50° C.

Yield: 328 g of colourless crystals (93% of theory)

According to NMR, the product obtained consists to about 22% of the desired title compound in a mixture with about 78% of the non-dehydrated intermediate 4-(chloromethyl)-2-[(4-fluorophenyl)amino]-4,5-dihydro-1,3-thiazol-4-ol. This product is further used as such, without further separation.

Method B: 600 mg (4.7 mmol) of 1,3-dichloroacetone and 768 mg (4.5 mmol) of 4-fluorophenylthiourea are dissolved in 10 ml of DMF and stirred at 80° C. for 4 h. 200 ml of water are added, and the mixture is extracted three times with ethyl acetate. The combined organic phases are washed with water and saturated aqueous sodium chloride solution, dried over sodium sulphate and concentrated to give a dark oil. This residue is chromatographed on 150 g of silica gel using isohexane→isohexane/ethyl acetate (10:1). The product is directly used further.

Yield: 714 mg (60% of theory)

LC-MS (Method 5): $R_t$=2.14 min; MS (ESIpos): m/z=243 [M+H]$^+$ $^1$H-NMR (400 MHz, DMSO-d$_6$): δ=10.28 (s, 1H); 7.69-7.62 (m, 2H); 7.20-7.12 (m, 2H); 6.94 (s, 1H); 4.67 (s, 2H).

Example 19A 4-(Chloromethyl)-2-(4-chlorophenyl)-1,3-thiazole

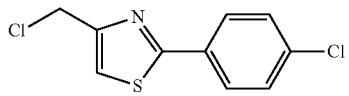 [SMILES: ClCc1csc(-c2ccc(Cl)cc2)n1]

The preparation is carried out as described in WO 03/053441 for Example 6.

Example 20A 4-(Chloromethyl)-2-(4-chlorophenyl)-1,3-oxazole

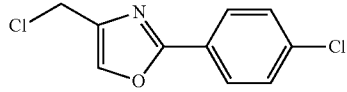 [SMILES: ClCc1coc(-c2ccc(Cl)cc2)n1]

1 g (6.43 mmol) of 4-chlorobenzamide is heated together with 816 mg of 1,3-dichloroacetone (6.43 mmol) at 135° C. for 1 h. The mixture is allowed to cool to RT, 1 ml of conc. sulphuric acid is added and the mixture is stirred for 5 min. The mixture is then poured onto ice, and the precipitate is filtered off with suction (946 mg). This precipitate is purified on 100 g of silica gel by column chromatography using a gradient of cyclohexane/ethyl acetate 20:1 to 5:1.

Yield: 532 mg (36% of theory)

LC-MS (Method 5): $R_t$=2.35 min; MS (ESIpos): m/z=228 [M+H]$^+$ $^1$H-NMR (400 MHz, DMSO-d$_6$): δ=8.31 (s, 1H), 8.0 (d, 2H), 7.62 (d, 2H), 4.75 (s, 2H).

Example 21A 4-(Chloromethyl)-2-(3,4-difluorophenyl)-1,3-thiazole

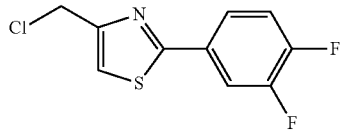 [SMILES: Fc1ccc(-c2nc(CCl)cs2)cc1F]

3.3 g (26 mmol) of 1,3-dichloroacetone and 4.5 g mg (26 mmol) of 3,4-difluorophenylthiourea are boiled in 45 ml of ethanol at reflux overnight. The solvent is evaporated under reduced pressure and the residue is purified by two silica gel chromatographics (cyclohexane/ethyl acetate 4:1 and isohexane/ethyl acetate 10:1).

Yield: 1.94 g (30% of theory)

LC-MS (Method 8): $R_t$=3.26 min; MS (ESIpos): no ionization $^1$H-NMR (400 MHz, DMSO-d$_6$): δ=8.03-7.94 (m, 1H), 7.88 (s, 1H), 7.84-7.80 (m, 1H), 7.63-7.54 (m, 1H), 4.89 (s, 2H).

Example 22A 4-(Hydroxymethyl)-N-methylpyridine-2-carboxamide

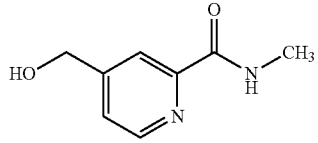

The preparation is carried out as described in U.S. Pat. No. 6,689,883 for intermediate H.

Example 23A 4-(Chloromethyl)-N-methylpyridine-2-carboxamide hydrochloride

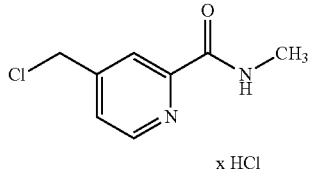

x HCl 10 g (45.32 mmol) of the compound from Example 22A are suspended in 160 ml of dichloromethane and cooled to 0° C. After addition of 16.18 g (135.96 mmol) of thionyl chloride, the reaction mixture is warmed to RT and stirred at RT overnight. The mixture is then concentrated by evaporation and the residue is dried under high vacuum.

Yield: 10 g (quant.)

LC-MS (Method 4): $R_t$=0.71 min; MS (ESIpos): m/z=185 [M+H]$^+$ $^1$H-NMR (400 MHz, DMSO-d$_6$): δ=8.85-8.78 (m, 1H), 8.65 (d, 1H), 8.10 (s, 1H), 7.64 (d, 1H), 4.90 (s, 2H), 2.83 (d, 3H).

Example 24A

4-{[(6-Amino-3,5-dicyano-4-phenylpyridin-2-yl)sulphanyl]methyl}-N-methylpyridine-2-carboxamide

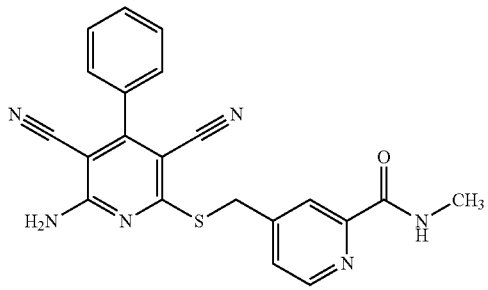 [SMILES: CNC(=O)c1cc(CSc2nc(N)c(C#N)c(-c3ccccc3)c2C#N)ccn1]

1 g (3.96 mmol) of 2-amino-4-phenyl-6-sulphanylpyridine-3,5-dicarbonitrile, 0.96 g (4.36 mmol) of 4-(chloromethyl)-N-methylpyridine-2-carboxamide hydrochloride and 1.33 g (15.84 mmol) of sodium bicarbonate are dissolved in 20 ml of DMF and stirred at RT for 2 h. 500 ml of water are added to the reaction mixture. The precipitate is filtered off and washed with water.

Yield: 1.42 g (90% of theory)

LC-MS (Method 3): $R_t$=1.74 min; MS (ESIpos): m/z=401 [M+H]$^+$.

$^1$H-NMR (400 MHz, DMSO-d$_6$): δ (400 MHz)=8.74 (q, 1H), 8.55 (d, 1H), 8.30-7.96 (s br, 2H), 8.15 (s, 1H), 7.80-7.75 (m, 1H), 7.58-7.50 (m, 5H), 4.60 (s, 2H), 2.81 (d, 3H).

Example 25A

4-{[(6-Chloro-3,5-dicyano-4-phenylpyridin-2-yl)thio]methyl}-N-methylpyridine-2-carboxamide

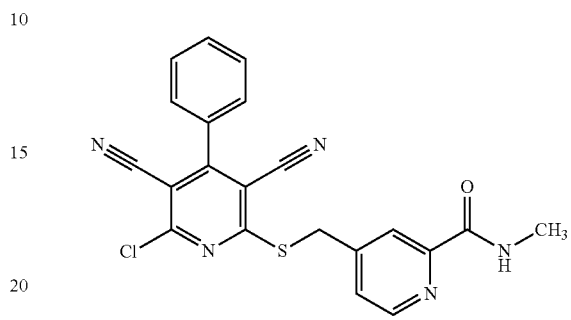

1.42 g (3.55 mmol) of the compound from Example 24A are initially charged in 30 ml of acetonitrile, 0.96 ml (7.10 mmol) of isopentyl nitrite and 0.95 g (7.10 mmol) of copper (II) chloride are added and the mixture is stirred at 60° C. for 5 hours. Once more, the same amount of copper(II) chloride is added and the mixture is stirred at 60° C. overnight. 7 ml of 1N hydrochloric acid are added, the mixture is extracted three times with ethyl acetate and the combined organic phases are washed with saturated aqueous sodium chloride solution, dried over sodium sulphate and concentrated. The residue is purified by preparative HPLC (with 0.1% TFA added).

Yield: 1.31 g (87% of theory)

LC-MS (Method 2): $R_t$=2.46 min; MS (ESIpos): m/z=420 [M+H]$^+$.

Example 26A

4-{[(4R)-2,2-Dimethyl-1,3-dioxolan-4-yl]methoxy}benzenecarbaldehyde

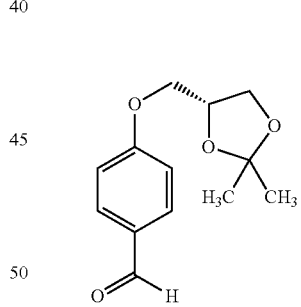

2 g (16.38 mmol) of p-methoxybenzaldehyde together with 3.7 g (24.57 mmol) of (4S)-4-(chloromethyl)-2,2-dimethyl-1,3-dioxolane and 15.8 g (114.64 mmol) of potassium carbonate are stirred in 10 ml of DMF at 130° C. overnight. The mixture is then added to water and extracted with methylene chloride. The organic phase is washed with saturated aqueous sodium chloride solution, dried over sodium sulphate and concentrated. The residue is purified on a silica gel column (mobile phase: cyclohexane/ethyl acetate 5:1). This gives 2.42 g (61% of theory) of the target compound.

$^1$H-NMR (400 MHz, DMSO-d$_6$): δ=9.87 (s, 1H), 7.87 (d, 2H), 7.15 (d, 2H), 4.47-4.41 (m, 1H), 4.19-4.15 (m, 1H), 4.13-4.08 (m, 2H), 3.79-3.75 (m, 1H), 1.36 (s, 3H), 1.31 (s, 3H).

LC-MS (Method 4): $R_t$=1.00 min; MS (ESIpos): m/z=237 [M+H]$^+$.

Example 27A

2-Amino-4-(4-{[(4R)-2,2-dimethyl-1,3-dioxolan-4-yl]methoxy}phenyl)-6-methoxypyridine-3,5-dicarbonitrile

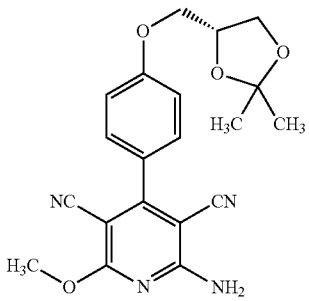 [SMILES: COc1nc(N)c(C#N)c(-c2ccc(OC[C@@H]3COC(C)(C)O3)cc2)c1C#N]

1.2 g (5.08 mmol) of 4-{[(4R)-2,2-dimethyl-1,3-dioxolan-4-yl]methoxy}benzenecarbaldehyde and 688 mg (10.41 mmol) of malononitrile are initially charged in 10 ml of methanol, 1.65 g (30.47 mmol) of sodium methoxide (30% strength, dissolved in methanol) are added and the mixture is stirred at room temperature for 2 hours. The precipitated solid is filtered off, washed with methanol and dried under high vacuum. This gives 451 mg (23% of theory) of the target compound.

$^1$H-NMR (400 MHz, DMSO-$d_6$): δ=7.92 (s, 2H), 7.47 (d, 2H), 7.13 (d, 2H), 4.47-4.41 (m, 1H), 4.14-4.05 (m, 3H), 3.96 (s, 3H), 3.80-3.75 (m, 1H), 1.37 (s, 3H), 1.32 (s, 3H).

LC-MS (Method 2): $R_t$=2.19 min; MS (ESIpos): m/z=381 [M+H]$^+$.

Example 28A

2-Chloro-4-(4-{[(2S)-2,3-dihydroxypropyl]oxy}phenyl)-6-methoxypyridine-3,5-dicarbonitrile

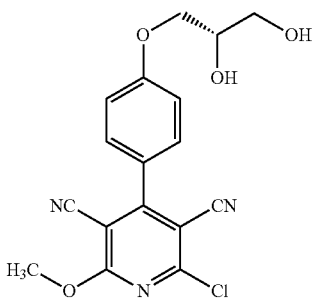 [SMILES: COc1nc(Cl)c(C#N)c(-c2ccc(OC[C@@H](O)CO)cc2)c1C#N]

450 mg (1.18 mmol) of 2-amino-4-(4-{[(4R)-2,2-dimethyl-1,3-dioxolan-4-yl]methoxy}phenyl)-6-methoxypyridine-3,5-dicarbonitrile together with 478 µl (3.55 mmol) of isoamyl nitrite and 477 mg (3.55 mmol) of copper(II) chloride are stirred in 10 ml of acetonitrile at 65° C. for 4 hours. The reaction mixture is purified by preparative HPLC (acetonitrile/water: 10:90→95:5). This gives 202 mg (44% of theory) of the target compound.

$^1$H-NMR (400 MHz, DMSO-$d_6$): δ=7.59 (d, 2H), 7.18 (d, 2H), 4.13 (s, 3H), 4.09 (d, 1H), 4.01-3.92 (m, 1H), 3.85-3.80 (m, 1H), 3.47 (d, 2H).

LC-MS (Method 4): $R_t$=1.02 min; MS (ESIneg): m/z=340 [M−H−H$_2$O]$^+$.

Example 29A 4-(4-{[(2S)-2,3-Dihydroxypropyl]oxy}phenyl)-2-methoxy-6-sulphanylpyridine-3,5-dicarbonitrile

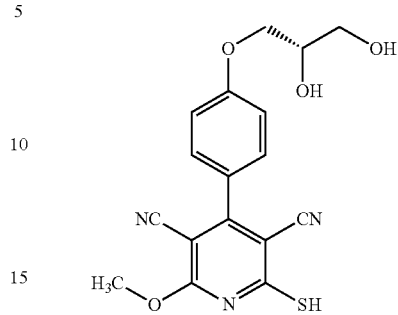

100 mg (0.278 mmol) of 2-chloro-4-(4-{[(2S)-2,3-dihydroxypropyl]oxy}phenyl)-6-methoxypyridine-3,5-dicarbonitrile are initially charged in 5 ml of DMF, 26 mg (0.334 mmol) of sodium sulphide are added and the mixture is stirred at room temperature for 4 hours. The reaction mixture is reacted further without any further purification.

LC-MS (Method 4): $R_t$=0.69 min; MS (ESIpos): m/z=358 [M+H]$^+$.

Example 30A

[2-(4-Chlorophenyl)-1,3-oxazol-4-yl]methanol

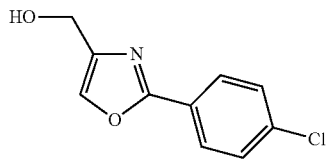 [SMILES: OCc1coc(-c2ccc(Cl)cc2)n1]

6 g (26.307 mmol) of 4-(chloromethyl)-2-(4-chlorophenyl)-1,3-oxazole were heated under reflux in 526 ml (52.613 mmol) of 0.1 N aqueous sodium hydroxide solution for 3 h. The mixture was then cooled to room temperature, and the precipitated solid was filtered off, washed with 0.1N aqueous sodium hydroxide solution and dried under high vacuum. This gave 4.79 g (85% of theory) of the target compound.

LC-MS (Method 4): $R_t$=0.94 min; MS (ESIpos): m/z=210 [M+H]$^+$.

WORKING EXAMPLES

Example 1

2-({[2-(4-Chlorophenyl)-1,3-thiazol-4-yl]methyl}sulphanyl)-4-phenyl-6-propoxypyridine-3,5-dicarbonitrile

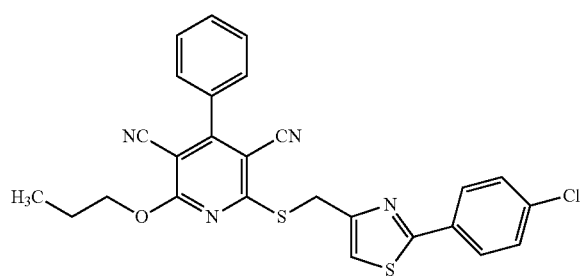 [SMILES: CCCOc1nc(SCc2csc(-c3ccc(Cl)cc3)n2)c(C#N)c(-c2ccccc2)c1C#N]

37 µl (0.501 mmol) of 1-propanol are initially charged in 2 ml of DMF, 20 mg (0.184 mmol) of potassium tert-butoxide are added and the mixture is stirred for 15 minutes, after which 100 mg (0.167 mmol) of 2-chloro-6-({[2-(4-chlorophenyl)-1,3-thiazol-4-yl]methyl}sulphanyl)-4-phenylpyridine-3,5-dicarbonitrile, dissolved in 2 ml of DMF, are added. The reaction mixture is stirred at room temperature for one hour and then purified by preparative HPLC (acetonitrile/water: 10:90→95:5, with 0.1% TFA added). This gives 13 mg (15% of theory) of the target compound.

$^1$H-NMR (400 MHz, DMSO-d$_6$): δ=7.95 (d, 2H), 7.74 (s, 1H), 7.62-7.57 (m, 7H), 4.79 (s, 2H), 4.53 (t, 2H), 1.79-1.70 (m, 2H), 0.93 (t, 3H).

LC-MS (Method 1): R$_t$=3.07 min; MS (ESIpos): m/z=503 [M+H]$^+$.

Example 2

2-({[2-(4-Chlorophenyl)-1,3-thiazol-4-yl]methyl}sulphanyl)-6-(3-hydroxypropoxy)-4-phenylpyridine-3,5-dicarbonitrile

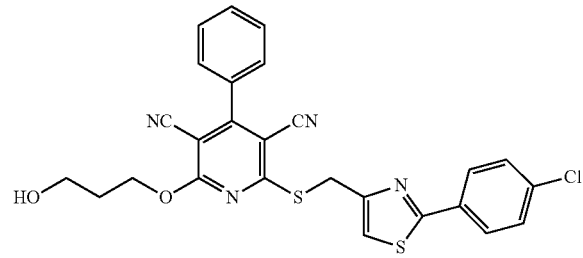 [SMILES: N#Cc1c(OCCCO)nc(SCc2csc(-c3ccc(Cl)cc3)n2)c(C#N)c1-c1ccccc1]

68 µl (0.939 mmol) of 1,3-propanediol are initially charged in 2 ml of DMF, 38 mg (0.344 mmol) of potassium tert-butoxide are added and the mixture is stirred for 15 minutes, after which 150 mg (0.313 mmol) of 2-chloro-6-({[2-(4-chlorophenyl)-1,3-thiazol-4-yl]methyl}sulphanyl)-4-phenylpyridine-3,5-dicarbonitrile, dissolved in 2 ml of DMF, are added. The reaction mixture is stirred at room temperature for 1 hour and then purified by preparative HPLC (acetonitrile/water: 10:90→95:5, with 0.1% TFA added). This gives 98 mg (59% of theory) of the target compound.

$^1$H-NMR (400 MHz, DMSO-d$_6$): δ=7.96 (d, 2H), 7.75 (s, 1H), 7.62-7.57 (m, 7H), 4.78 (s, 2H), 4.68 (t, 2H), 3.55 (t, 2H), 1.94-1.87 (m, 2H).

LC-MS (Method 2): R$_t$=2.90 min; MS (ESIpos): m/z=519 [M+H]$^+$.

Example 3

2-({[2-(4-Chlorophenyl)-1,3-thiazol-4-yl]methyl}sulphanyl)-4-[4-(2-hydroxyethoxy)phenyl]-6-(3-hydroxypropoxy)pyridine-3,5-dicarbonitrile

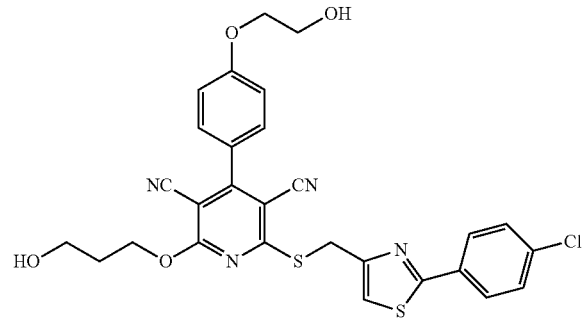 [SMILES: N#Cc1c(OCCCO)nc(SCc2csc(-c3ccc(Cl)cc3)n2)c(C#N)c1-c1ccc(OCCO)cc1]

The preparation is carried out analogously to Example 2 from Example 4A.

$^1$H-NMR (400 MHz, DMSO-d$_6$): δ=7.97 (d, 2H), 7.74 (s, 1H), 7.60-7.52 (m, 4H), 7.15 (d, 2H), 4.91 (br s, 1H), 4.80 (s, 2H), 4.70-4.58 (m, 3H), 4.09 (t, 2H), 3.74 (t, 2H), 3.54 (t, 2H), 1.90 (quintet, 2H).

LC-MS (Method 4): R$_t$=1.36 min; MS (ESIpos): m/z=579 [M+H]$^+$.

Example 4

2-({[2-(4-Chlorophenyl)-1,3-thiazol-4-yl]methyl}sulphanyl)-4-[4-(2-hydroxyethoxy)phenyl]-6-(2-methylpropoxy)pyridine-3,5-dicarbonitrile

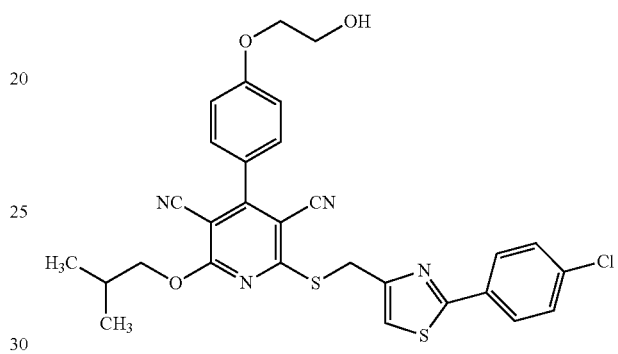

The preparation is carried out analogously to Example 2 from Example 4A.

$^1$H-NMR (400 MHz, DMSO-d$_6$): δ=7.97 (d, 2H), 7.71 (s, 1H), 7.61-7.53 (m, 4H), 7.15 (d, 2H), 4.92 (t, 1H), 4.79 (s, 2H), 4.30 (d, 2H), 4.09 (t, 2H), 3.74 (q, 2H), 2.05 (septet, 1H), 0.91 (d, 6H).

LC-MS (Method 3): R$_t$=2.76 min; MS (ESIpos): m/z=577 [M+H]$^+$.

Example 5

2-({[2-(4-Chlorophenyl)-1,3-thiazol-4-yl]methyl}sulphanyl)-6-[(1-methylpyrrolidin-3-yl)oxy]-4-phenylpyridine-3,5-dicarbonitrile

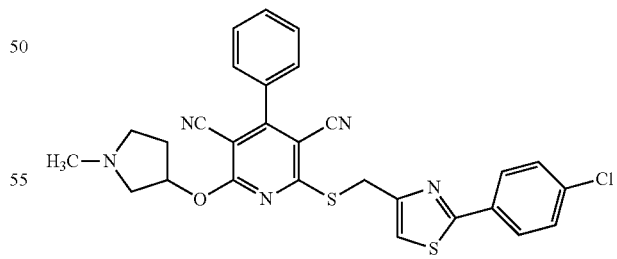

25 µl (0.229 mmol) of 3-hydroxy-N-methylpyrrolidine are initially charged in 0.5 ml of THF, the mixture is cooled to 0° C., 249 µl (0.249 mmol) of phosphazene base P(4)-t-Bu (1M in THF) are added and the mixture is stirred at this temperature for 10 minutes. 120 mg (0.208 mmol) of the compound from Example 3A are then added, and the mixture is stirred at RT overnight. The reaction mixture is then purified by preparative HPLC (addition of 0.15% hydrochloric acid). This gives 38 mg of the impure target compound. This is dissolved in dichloromethane and washed twice with 1N hydrochloric acid, once with water and once with saturated aqueous sodium chloride solution. After drying over sodium sulphate, the organic phase is concentrated on a rotary evaporator and the crude product is purified once more by preparative HPLC (addition of 0.15% hydrochloric acid).

Yield: 7 mg (6% of theory)

$^1$H-NMR (400 MHz, DMSO-$d_6$): δ=10.40 (br s, 1H), 7.98 (d, 2H), 7.80 (d, 1H), 7.65-7.58 (m, 7H), 5.96-5.87 (m, 1H), 4.82 (s, 2H), 4.10-3.83 (m, 1H), 3.78-3.68 (m, 1H), 3.58-3.42 (m, 1H), 3.30-3.09 (m, 1H), 2.89 (d, 3H), 2.44-2.18 (m, 2H).

LC-MS (Method 2): $R_t$=2.00 min; MS (ESIpos): m/z=544 [M+H]$^+$.

Example 6

2-({[2-(4-Chlorophenyl)-1,3-thiazol-4-yl]methyl}sulphanyl)-6-(3-hydroxypropoxy)-4-(1,3-thiazol-5-yl)pyridine-3,5-dicarbonitrile

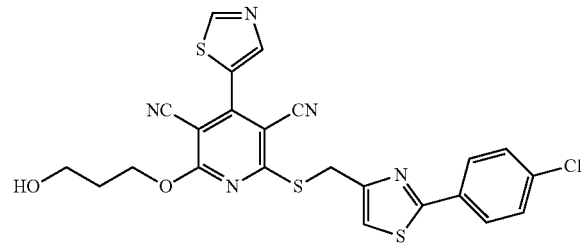 [SMILES: N#Cc1c(OCCCO)nc(SCc2csc(-c3ccc(Cl)cc3)n2)c(C#N)c1-c1cncs1]

30 μl (0.419 mmol) of 1,3-propanediol are initially charged in 2 ml of DMF, 18 mg (0.154 mmol) of potassium tert-butoxide are added and the mixture is stirred for 15 minutes, after which 75 mg (0.14 mmol) of 2-chloro-6-({[2-(4-chlorophenyl)-1,3-thiazol-4-yl]methyl}sulphanyl)-4-(1,3-thiazol-5-yl)pyridine-3,5-dicarbonitrile, dissolved in 2 ml of DMF, are added. The reaction mixture is stirred at room temperature for 30 minutes and then purified by preparative HPLC (acetonitrile/water: 10:90→95:5). This gives 11 mg (15% of theory) of the target compound.

$^1$H-NMR (400 MHz, DMSO-$d_6$): δ=9.45 (d, 1H), 8.38 (d, 1H), 7.95 (d, 2H), 7.74 (s, 1H), 7.58 (d, 2H), 4.81 (s, 2H), 4.68 (t, 2H), 4.64 (t, 1H), 3.53 (q, 2H), 1.93-1.87 (m, 2H).

LC-MS (Method 3): $R_t$=2.22 min; MS (ESIpos): m/z=526 [M+H]$^+$.

Example 7

2-({[2-(4-Chlorophenyl)-1,3-oxazol-4-yl]methyl}sulphanyl)-4-[4-(2-hydroxyethoxy)phenyl]-6-methoxypyridine-3,5-dicarbonitrile

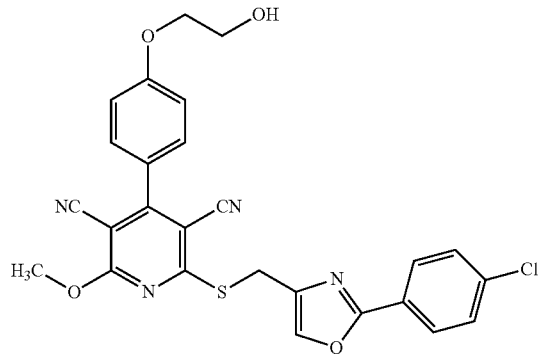 [SMILES: COc1nc(SCc2coc(-c3ccc(Cl)cc3)n2)c(C#N)c(-c2ccc(OCCO)cc2)c1C#N]

400 mg (1.222 mmol) of 4-[4-(2-hydroxyethoxy)phenyl]-2-methoxy-6-sulphanylpyridine-3,5-dicarbonitrile together with 306 mg (1.344 mmol) of 4-(chloromethyl)-2-(4-chlorophenyl)-1,3-oxazole and 410 mg (4.888 mmol) of sodium bicarbonate in 8 ml of DMF are stirred at room temperature overnight. The reaction mixture is purified by preparative HPLC (acetonitrile/water: 10:90→95:5). This gives 10.4 mg (1.6% of theory) of the target compound.

$^1$H-NMR (400 MHz, DMSO-$d_6$): δ=8.21 (s, 1H), 7.97 (d, 2H), 7.61 (d, 2H), 7.54 (d, 2H), 7.14 (d, 2H), 4.87 (t, 1H), 4.63 (s, 2H), 4.21 (s, 3H), 4.09 (t, 2H), 3.75 (m, 2H).

LC-MS (Method 4): $R_t$=1.39 min; MS (ESIpos): m/z=519 [M+H]$^+$.

Example 8

2-({[2-(4-Chlorophenyl)-1,3-thiazol-4-yl]methyl}sulphanyl)-4-[4-(2-hydroxyethoxy)phenyl]-6-methoxypyridine-3,5-dicarbonitrile

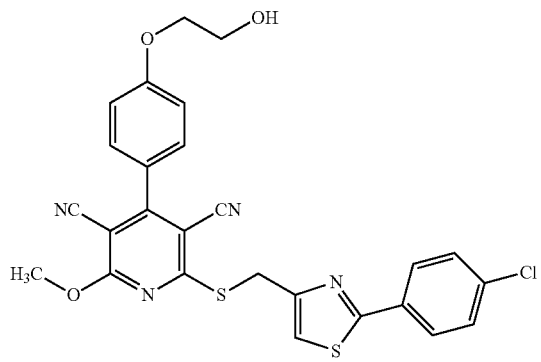 [SMILES: COc1nc(SCc2csc(-c3ccc(Cl)cc3)n2)c(C#N)c(-c2ccc(OCCO)cc2)c1C#N]

2.095 g (6.399 mmol) of 4-[4-(2-hydroxyethoxy)phenyl]-2-methoxy-6-sulphanylpyridine-3,5-dicarbonitrile together with 1.875 g (7.679 mmol) of 4-(chloromethyl)-2-(4-chlorophenyl)-1,3-thiazole and 1.613 g (19.197 mmol) of sodium bicarbonate in 50 ml of DMF are stirred at room temperature overnight. Water and methanol are added, and the reaction mixture is placed in an ultrasonic bath for 2 minutes. A white solid precipitates out and is filtered off, washed with methanol and dried under high vacuum. The mother liquor is concentrated to half of the original volume and placed in the fridge for 30 minutes. The precipitated solid is filtered off, washed with methanol and dried under high vacuum. The two precipitated solids are combined, giving a total of 2.98 g (85% of theory) of the target compound.

$^1$H-NMR (400 MHz, DMSO-$d_6$): δ=7.95 (d, 2H), 7.76 (s, 1H), 7.63-7.53 (m, 4H), 7.15 (d, 2H), 4.93 (s br, 1H), 4.82 (s, 2H), 4.18 (s, 3H), 4.09 (t, 2H), 3.75 (t br, 2H).

LC-MS (Method 3): $R_t$=2.45 min; MS (ESIpos): m/z=535 [M+H]$^+$.

Example 9

3-[({3,5-Dicyano-4-[4-(2-hydroxyethoxy)phenyl]-6-methoxypyridin-2-yl}thio)methyl]benzoic acid

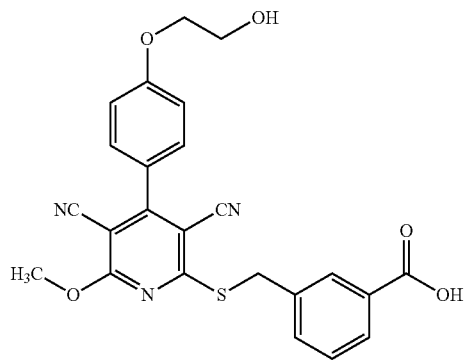 [SMILES: COc1nc(SCc2cccc(C(=O)O)c2)c(C#N)c(-c2ccc(OCCO)cc2)c1C#N]

50 mg (0.153 mmol) of the compound from Example 10A together with 29 mg (0.168 mmol) of 3-(chloromethyl)benzoic acid and 38.5 mg (0.458 mmol) of sodium bicarbonate are stirred in 0.6 ml of DMF at room temperature for 2 h. Water is added and the reaction mixture is purified by preparative HPLC (with 0.15% hydrochloric acid added).

Yield: 28 mg (39% of theory)

$^1$H-NMR (400 MHz, DMSO-$d_6$): δ=13.05 (s br, 1H), 8.11 (s, 1H), 7.84 (d, 1H), 7.76 (d, 1H), 7.56 (d, 2H), 7.50 (t, 1H), 7.13 (d, 2H), 4.73 (s, 2H), 4.18 (s, 3H), 4.09 (t, 2H), 3.80 (br s, 1H), 3.74 (t, 2H).

LC-MS (Method 9): $R_t$=3.28 min; MS (ESIpos): m/z=462 [M+H]+.

Example 10

3-{[(3,5-Dicyano-6-methoxy-4-phenylpyridin-2-yl)thio]methyl}benzoic acid

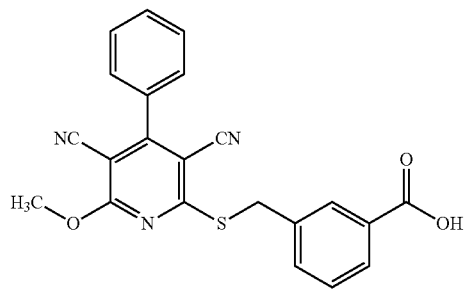 [SMILES: COc1nc(SCc2cccc(C(=O)O)c2)c(C#N)c(-c2ccccc2)c1C#N]

75 mg (0.177 mmol) of the compound from Example 11A together with 33 mg (0.194 mmol) of 3-(chloromethyl)benzoic acid and 44.5 mg (0.530 mmol) of sodium bicarbonate are stirred in 1.0 ml of DMF at room temperature overnight. Water is added and the reaction mixture is purified by preparative HPLC (with 0.15% hydrochloric acid added).

Yield: 67 mg (94% of theory)

$^1$H-NMR (400 MHz, DMSO-$d_6$): δ=13.08 (s br, 1H), 8.12 (s, 1H), 7.86 (d, 1H), 7.76 (d, 1H), 7.62-7.56 (m, 5H), 7.50 (t, 1H), 4.75 (s, 2H), 4.19 (s, 3H).

LC-MS (Method 10): $R_t$=3.50 min; MS (ESIpos): m/z=402 [M+H]+.

Example 11

4-[4-(2-Hydroxyethoxy)phenyl]-2-methoxy-6-[(3-methoxybenzyl)sulphanyl]pyridine-3,5-dicarbonitrile

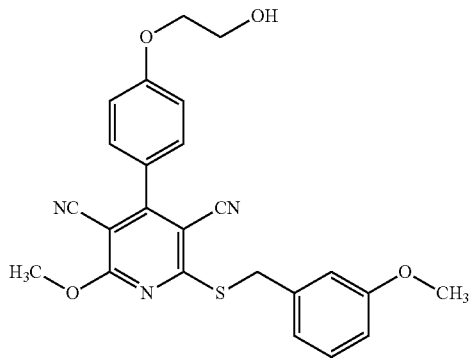

75 mg (0.229 mmol) of 4-[4-(2-hydroxyethoxy)phenyl]-2-methoxy-6-sulphanylpyridine-3,5-dicarbonitrile together with 36 µl (0.253 mmol) of 3-methoxybenzyl bromide and 52 mg (0.380 mmol) of potassium carbonate are stirred in 1 ml of DMF at room temperature overnight. The reaction mixture is purified by preparative HPLC (acetonitrile/water: 10:90→95:5, with 0.1% formic acid added). This gives 16 mg (56% of theory) of the target compound.

$^1$H-NMR (400 MHz, DMSO-$d_6$): δ=7.56 (d, 2H), 7.28 (t, 1H), 7.15 (d, 2H), 7.07-7.06 (m, 2H), 6.88 (m, 1H), 4.95 (t, 1H), 4.65 (s, 2H), 4.17 (s, 3H), 4.10 (t, 2H), 3.75 (m, 2H).

LC-MS (Method 5): $R_t$=2.39 min; MS (ESIpos): m/z=448 [M+H]+.

Example 12

4-[4-(2-Hydroxyethoxy)phenyl]-2-methoxy-6-[(pyridin-3-ylmethyl)sulphanyl]pyridine-3,5-dicarbonitrile

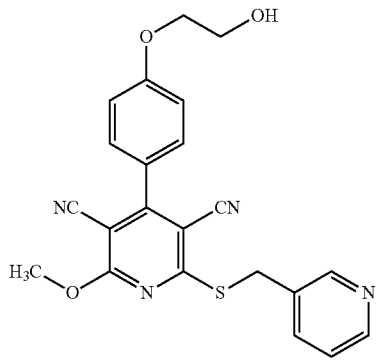 [SMILES: COc1nc(SCc2cccnc2)c(C#N)c(-c2ccc(OCCO)cc2)c1C#N]

494 mg (1.5 mmol) of 2-chloro-4-[4-(2-hydroxyethoxy)phenyl]-6-methoxypyridine-3,5-dicarbonitrile are initially charged in 5 ml of DMF, 140 mg (1.8 mmol) of sodium sulphide are added and the mixture is stirred at room temperature for 3 hours. 311 mg (2.25 mmol) of potassium carbonate and 307 mg (1.8 mmol) of 3-picolyl chloride hydrochloride are then added. The reaction mixture is stirred at 45° C. overnight and then purified by preparative HPLC (acetonitrile/water: 10:90→95:5, with 0.1% formic acid added). This gives 255 mg (40% of theory) of the target compound.

¹H-NMR (400 MHz, DMSO-d₆): δ=8.71 (s, 1H), 8.50 (d, 1H), 7.90 (d, 1H), 7.54 (d, 2H), 7.40 (dd, 1H), 7.14 (d, 2H), 4.70 (s, 2H), 4.13 (s, 3H), 4.10 (t, 2H), 3.75 (m, 2H).

LC-MS (Method 5): $R_t$=1.63 min; MS (ESIpos): m/z=419 [M+H]⁺.

Example 13

2-[({2-[(4-Fluorophenyl)amino]-1,3-thiazol-4-yl}methyl)sulphanyl]-4-[4-(2-hydroxyethoxy)phenyl]-6-methoxypyridine-3,5-dicarbonitrile

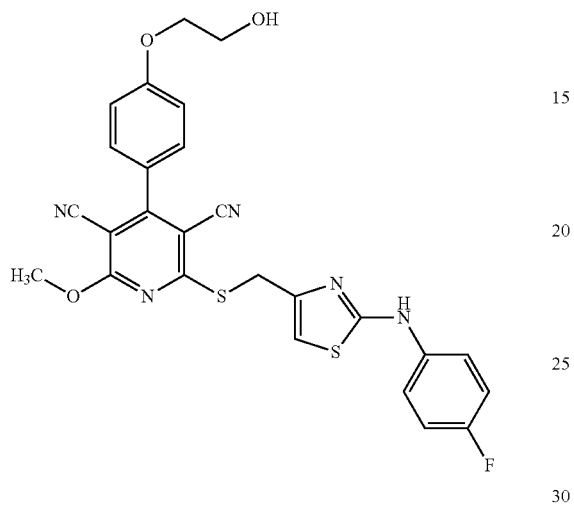

122 mg (0.371 mmol) of 4-[4-(2-hydroxyethoxy)phenyl]-2-methoxy-6-sulphanylpyridine-3,5-dicarbonitrile are dissolved in 3 ml of DMF and 1 ml of ethanol, 118 mg (0.397 mmol) of the compound from Example 18A (Method A), 130 mg (0.94 mmol) of potassium carbonate and 20 mg (0.53 mmol) of sodium borohydride are added and the mixture is stirred at 50° C. overnight. After addition of 0.4 ml of 5N acetic acid, the product is purified by preparative HPLC (acetonitrile/water: 10:90→95:5, with 0.1% formic acid added). This gives 59 mg (30% of theory) of the target compound.

¹H-NMR (400 MHz, DMSO-d₆): δ=10.27 (s, 1H), 7.61-7.59 (m, 1H), 7.55 (d, 2H), 7.15 (d, 2H), 7.12 (t, 2H), 6.86 (s, 1H), 4.93 (t, 1H), 4.61 (s, 2H), 4.19 (s, 3H), 4.09 (t, 2H), 3.74 (q, 2H).

LC-MS (Method 5): $R_t$=2.42 min; MS (ESIpos): m/z=534 [M+H]⁺.

Example 14

2-({[2-(3,4-Difluorophenyl)-1,3-thiazol-4-yl]methyl}sulphanyl)-4-[4-(2-hydroxyethoxy)phenyl]-6-methoxypyridine-3,5-dicarbonitrile

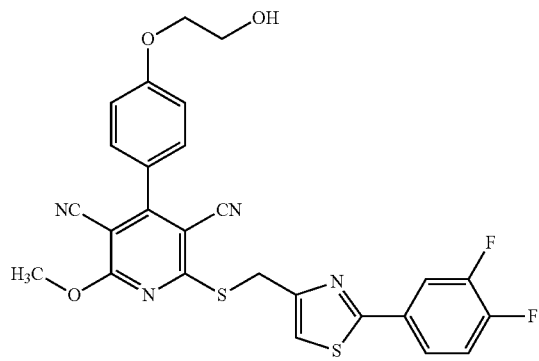 [SMILES: COc1nc(SCc2csc(-c3ccc(F)c(F)c3)n2)c(C#N)c(-c2ccc(OCCO)cc2)c1C#N]

36 mg (0.111 mmol) of 2-chloro-4-[4-(2-hydroxyethoxy)phenyl]-6-methoxypyridine-3,5-dicarbonitrile are initially charged in 1 ml of DMF, 34 mg (0.138 mmol) of 4-(chloromethyl)-2-(3,4-difluorophenyl)-1,3-thiazole and 28 mg (0.332 mmol) of sodium bicarbonate are added and the mixture is stirred at room temperature overnight. The reaction mixture is purified by preparative HPLC (acetonitrile/water: 10:90→95:5, with 0.1% formic acid added). This gives 33 mg (48% of theory) of the target compound.

¹H-NMR (400 MHz, DMSO-d₆): δ=7.99-7.95 (m, 1H), 7.80-7.77 (m, 2H), 7.61-7.57 (m, 1H), 7.15 (d, 2H), 4.93 (t, 1H), 4.81 (s, 2H), 4.18 (s, 3H), 4.09 (t, 2H), 3.75 (q, 2H).

LC-MS (Method 11): $R_t$=2.80 min; MS (ESIpos): m/z=537 [M+H]⁺.

Example 15

2-({[2-(4-Chlorophenyl)-1,3-oxazol-4-yl]methyl}sulphanyl)-6-ethoxy-4-[4-(2-hydroxyethoxy)-phenyl]pyridine-3,5-dicarbonitrile

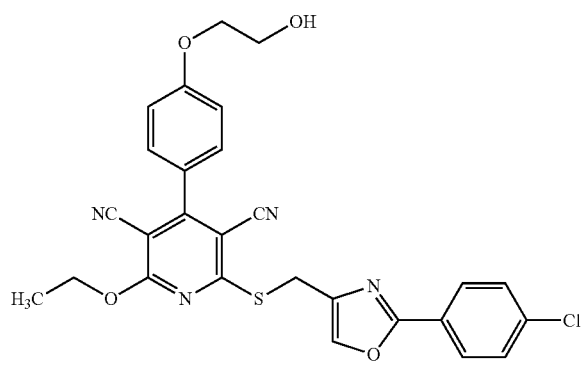 [SMILES: CCOc1nc(SCc2coc(-c3ccc(Cl)cc3)n2)c(C#N)c(-c2ccc(OCCO)cc2)c1C#N]

100 mg (0.293 mmol) of 2-ethoxy-4-[4-(2-hydroxyethoxy)phenyl]-6-sulphanylpyridine-3,5-dicarbonitrile together with 73 mg (0.322 mmol) of 4-(chloromethyl)-2-(4-chlorophenyl)-1,3-oxazole and 98 mg (1.172 mmol) of sodium bicarbonate are stirred in 2 ml of DMF at room temperature overnight. The reaction mixture is purified by preparative HPLC (acetonitrile/water: 10:90→95:5). This gives 41.5 mg (26% of theory) of the target compound.

¹H-NMR (400 MHz, DMSO-d₆): δ=8.23 (s, 1H), 7.96 (d, 2H), 7.62 (d, 2H), 7.56 (d, 2H), 7.16 (d, 2H), 4.92 (s, 1H), 4.66 (m, 2H), 4.60 (s, 2H), 4.09 (m, 2H), 3.75 (m, 2H), 1.38 (m, 3H).

LC-MS (Method 4): $R_t$=1.45 min; MS (ESIpos): m/z=533 [M+H]⁺.

Example 16

2-({[2-(4-Chlorophenyl)-1,3-thiazol-4-yl]methyl}sulphanyl)-6-ethoxy-4-[4-(2-hydroxyethoxy)-phenyl]pyridine-3,5-dicarbonitrile

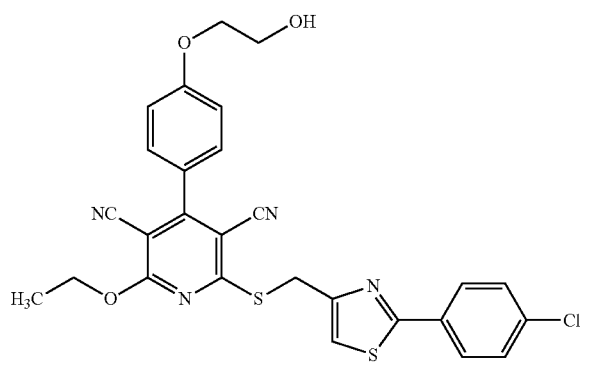 [SMILES: CCOc1nc(SCc2csc(-c3ccc(Cl)cc3)n2)c(C#N)c(-c2ccc(OCCO)cc2)c1C#N]

100 mg (0.293 mmol) of 2-ethoxy-4-[4-(2-hydroxyethoxy)phenyl]-6-sulphanylpyridine-3,5-dicarbonitrile together with 78 mg (0.322 mmol) of 4-(chloromethyl)-2-(4-chlorophenyl)-1,3-thiazole and 98 mg (1.172 mmol) of sodium bicarbonate are stirred in 2 ml of DMF at room temperature overnight. The reaction mixture is purified by preparative HPLC (acetonitrile/water: 10:90→95:5). This gives 77 mg (47% of theory) of the target compound.

$^1$H-NMR (400 MHz, DMSO-$d_6$): δ=7.95 (d, 2H), 7.74 (s, 1H), 7.58 (d, 2H), 7.55 (d, 2H), 7.14 (d, 2H), 4.92 (t, 1H), 4.78 (s, 2H), 4.63 (q, 2H), 4.09 (t, 2H), 3.75 (q, 2H), 1.34 (t, 3H).

LC-MS (Method 4): $R_t$=1.51 min; MS (ESIpos): m/z=549 [M+H]$^+$.

Example 17

2-({[2-(4-Chlorophenyl)-1,3-oxazol-4-yl]methyl}sulphanyl)-4-(4-hydroxyphenyl)-6-methoxypyridine-3,5-dicarbonitrile

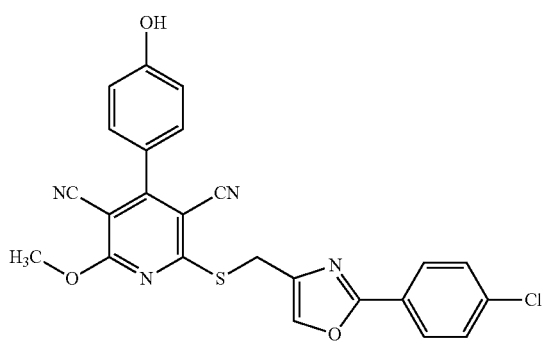 [SMILES: COc1nc(SCc2coc(-c3ccc(Cl)cc3)n2)c(C#N)c(-c2ccc(O)cc2)c1C#N]

64 mg (0.224 mmol) of 4-(4-hydroxyphenyl)-2-methoxy-6-sulphanylpyridine-3,5-dicarbonitrile together with 88 mg (0.269 mmol) of 4-(chloromethyl)-2-(4-chlorophenyl)-1,3-oxazole and 57 mg (0.672 mmol) of sodium bicarbonate are stirred in 2 ml of DMF at room temperature overnight. The reaction mixture is purified by preparative HPLC (acetonitrile/water: 10:90→95:5, with 0.1% TFA added). This gives 44 mg (41% of theory) of the target compound.

$^1$H-NMR (400 MHz, DMSO-$d_6$): δ=10.2 (s, 1H), 8.23 (s, 1H), 7.97 (d, 2H), 7.61 (d, 2H), 7.44 (d, 2H), 6.95 (d, 2H), 4.62 (s, 2H), 4.20 (s, 3H).

LC-MS (Method 4): $R_t$=1.43 min; MS (ESIpos): m/z=475 [M+H]$^+$.

Example 18

4-({[3,5-Dicyano-6-(2-hydroxyethoxy)-4-phenylpyridin-2-yl]thio}methyl)-N-methylpyridine-2-carboxamide

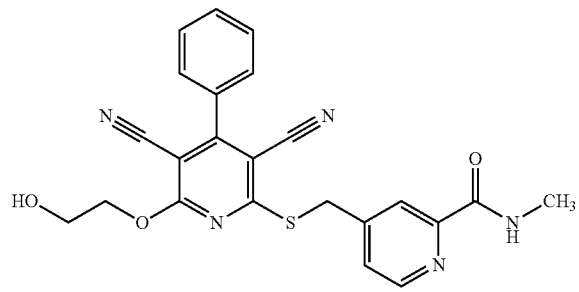 [SMILES: CNC(=O)c1cc(CSc2nc(OCCO)c(C#N)c(-c3ccccc3)c2C#N)ccn1]

22 mg (0.357 mmol) of 1,2-ethanediol are initially charged in 0.5 ml of DMF, and 4.8 mg (0.179 mmol) of sodium hydride are added. After 15 min at RT, 50 mg (0.119 mmol) of the compound from Example 25A are added and the reaction mixture is stirred at 115° C. overnight. After cooling, the reaction solution is purified by prep. HPLC.

Yield: 19 mg (28% of theory)

$^1$H-NMR (400 MHz, DMSO-$d_6$): δ=8.79 (q, 1H), 8.58 (d, 1H), 8.10 (d, 1H), 7.70-7.58 (m, 6H), 4.69 (br s, 1H), 4.56 (t, 2H), 3.80 (t, 2H), 2.82 (d, 3H).

LC-MS (Method 1): $R_t$=1.95 min; MS (ESIpos): m/z=446 [M+H]$^+$.

The examples listed in Table 1 are prepared from the appropriate starting materials analogously to Example 18 with subsequent purification:

TABLE 1
| Example No. | Structure (yield) | LC-MS: R$_t$ [min] (Method); MS (ESI): m/z [M + H]$^+$ | $^1$H-NMR (DMSO-d$_6$): |
|---|---|---|---|
| 19 | 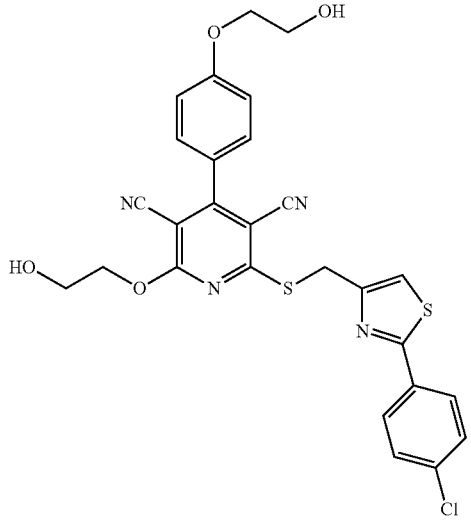 [SMILES: N#Cc1c(OCCO)nc(SCc2csc(-c3ccc(Cl)cc3)n2)c(C#N)c1-c1ccc(OCCO)cc1]<br>(12% of theory) | 2.12 min (Method 3); m/z = 565 | δ (400 MHz) = 7.97 (d, 2H), 7.74 (s, 1H), 7.59-7.52 (m, 4H), 7.15 (d, 2H), 4.98 (t, 1H), 4.91 (t, 1H), 4.79 (s, 2H), 4.63 (t, 2H), 4.09 (t, 2H), 3.78-3.70 (m, 4H). |
| 20 | 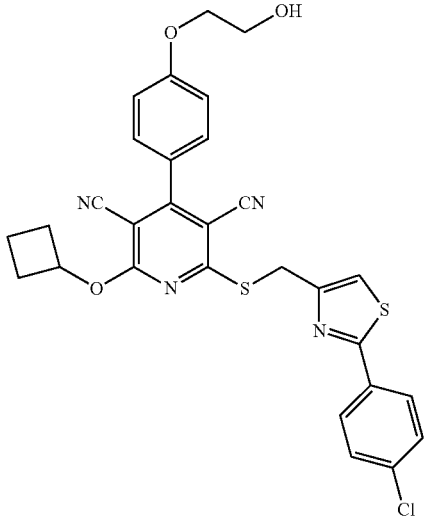 [SMILES: N#Cc1c(OC2CCC2)nc(SCc2csc(-c3ccc(Cl)cc3)n2)c(C#N)c1-c1ccc(OCCO)cc1]<br>(30% of theory) | 3.17 min (Method 2); m/z = 575 | δ (400 MHz) = 7.98 (d, 2H), 7.74 (s, 1H), 7.61-7.53 (m, 4H), 7.14 (d, 2H), 5.37 (quintet, 1H), 4.79 (s, 2H), 4.09 (t, 2H), 3.73 (t, 2H), 2.44-2.32 (m, 2H), 2.23-2.10 (m, 2H), 1.85-1.75 (m, 1H), 1.68-1.53 (m, 1H). |

Example 21

Formic acid 4-[4-(2-hydroxyethoxy)phenyl]-2-[(1H-imidazol-4-ylmethyl)sulphanyl]-6-methoxypyridine-3,5-dicarbonitrile (1:1)

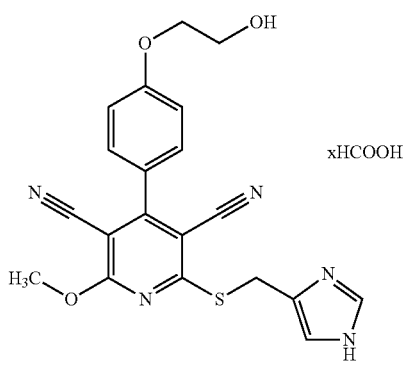 [SMILES: COc1nc(SCc2c[nH]cn2)c(C#N)c(-c2ccc(OCCO)cc2)c1C#N]

The compound is prepared analogously to the procedure for Example 14 from 2-chloro-4-[4-(2-hydroxyethoxy)phenyl]-6-methoxypyridine-3,5-dicarbonitrile and 4-chloromethylimidazole.

Yield 3.8 mg (7% of theory)

$^1$H-NMR (500 MHz, DMSO-$d_6$): δ=8.12 (s, 1H) 7.61 (s, 1H), 7.54 (d, 2H), 7.18-7.00 (m, 3H), 4.92 (t, 1H), 4.58 (s, 2H), 4.18 (s, 3H), 4.20 (s, 3H) 4.10 (t, 2H), 3.73 (q, 2H).

LC-MS (Method 11): $R_t$=2.24 min; MS (ESIpos): m/z=408 [M+H]$^+$.

Example 22

2-({[2-(4-Chlorophenyl)-1,3-thiazol-4-yl]methyl}sulphanyl)-4-(4-{[(2S)-2,3-dihydroxypropyl]-oxy}phenyl)-6-methoxypyridine-3,5-dicarbonitrile

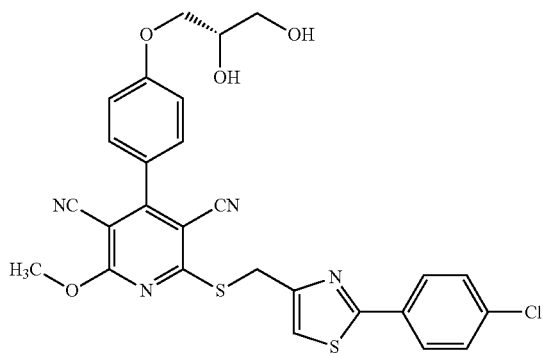 [SMILES: COc1nc(SCc2csc(-c3ccc(Cl)cc3)n2)c(C#N)c(-c2ccc(OC[C@@H](O)CO)cc2)c1C#N]

The solution from Example 29A is stirred together with 75 mg (0.306 mmol) of 4-(chloromethyl)-2-(4-chlorophenyl)-1,3-thiazole and 93 mg (1.112 mmol) of sodium bicarbonate at room temperature overnight. The reaction mixture is purified by preparative HPLC (acetonitrile/water: 10:90→95:5, with 0.1% TFA added). This gives 33 mg (20% of theory over two steps) of the target compound.

$^1$H-NMR (400 MHz, DMSO-$d_6$): δ=7.95 (d, 2H), 7.76 (s, 1H), 7.57 (dd, 4H), 7.14 (d, 2H), 5.05 (d, 1H), 4.82 (s, 2H), 4.70 (t, 1H), 4.18 (s, 3H), 4.12-4.08 (m, 1H), 4.00-3.95 (m, 1H), 3.85-3.79 (m, 1H), 3.46 (t, 2H).

LC-MS (Method 4): $R_t$=1.41 min; MS (ESIpos): m/z=565 [M+H]$^+$.

Example 23

2-{[2-(4-Chlorophenyl)-1,3-oxazol-4-yl]methoxy}-4-[4-(2-hydroxyethoxy)phenyl]-6-methoxypyridine-3,5-dicarbonitrile

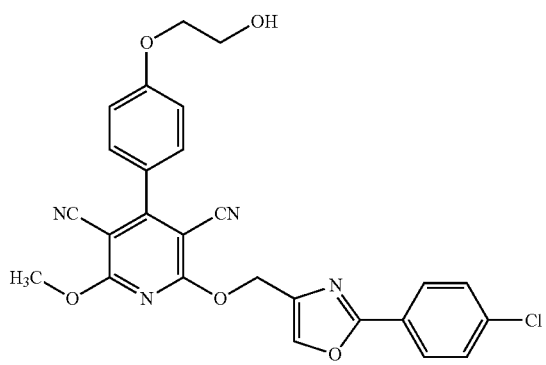 [SMILES: COc1nc(OCc2coc(-c3ccc(Cl)cc3)n2)c(C#N)c(-c2ccc(OCCO)cc2)c1C#N]

190 mg (0.910 mmol) of [2-(4-chlorophenyl)-1,3-oxazol-4-yl]methanol are initially charged in 2 ml of DMF, 37 mg (0.334 mmol) of potassium 2-methylpropan-2-oxide are added and the mixture is stirred at room temperature for 20 min. 100 mg (0.303 mmol) of 2-chloro-4-[4-(2-hydroxyethoxy)phenyl]-6-methoxypyridine-3,5-dicarbonitrile, dissolved in 1 ml of DMF, are then added. The mixture is stirred at room temperature overnight, and the product is then isolated by preparative HPLC (acetonitrile/water: 10:90→95:5, with 0.1% TFA added). This gives 31 mg (20% of theory) of the target compound.

$^1$H-NMR (400 MHz, DMSO-$d_6$): δ=8.44 (s, 1H), 8.01 (d, 2H), 7.63 (d, 2H), 7.54 (d, 2H), 7.15 (d, 2H), 5.62 (s, 2H), 4.19 (s, 3H), 4.09 (t, 2H), 3.75 (t, 2H).

LC-MS (Method 3): $R_t$=2.23 min; MS (ESIpos): m/z=503 [M+H]$^+$.

B. ASSESSING THE PHARMACOLOGICAL AND PHYSIOLOGICAL ACTIVITY

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. Test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5\times10^{-11}$ M to $3\times10^{-6}$ M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiotreitol (DTT), pH 7.8) and 50% luciferase substrate solution (2.5 mM ATP, 0.5 mM luciferin, 0.1 mM coenzyme A, 10 mM tricine, 1.35 mM magnesium sulphate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase response is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357, 1-9 (1998)).

Table 1 below lists the $EC_{50}$ values of representative working examples for the receptor stimulation on adenosine A1, A2a and A2b receptor subtypes:

TABLE 6

| Example No. | EC50 A1 [nM] (1 µM forskolin) | EC50 A2a [nM] | EC50 A2b [nM] |
|---|---|---|---|
| 1 | 1.3 | 3000 | 3000 |
| 2 | 0.7 | 3000 | 534 |
| 3 | 0.6 | 689 | 263 |
| 6 | 5.7 | 3000 | 3000 |
| 8 | 0.3 | 1220 | 105 |
| 11 | 0.8 | 1110 | 3000 |
| 12 | 1.2 | 547 | 3000 |
| 15 | 4.8 | 3000 | 3000 |
| 16 | 0.8 | 527 | 3000 |
| 18 | 0.3 | 1740 | 3000 |
| 19 | 0.5 | 685 | 177 |
| 21 | 73.2 | 3000 | 28.6 |
| 22 | 2.1 | 1260 | 142 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the decrease in the contraction of the vessels is measured. A decrease in contraction corresponds to dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters). Blood pressure, heart rate and their changes are then recorded over a period of 24 hours.

B-4. Measurement of Blood Pressure and Heart Rate on Awake Marmosets

Various concentrations of test substances are administered orally to awake marmosets which carry an internal transmitter capable of measuring permanently both blood pressure and heart rate (telemetric monitoring of hemodynamic parameters). Blood pressure, heart rate and their changes are then recorded over a period of 6-24 hours.

B-5. Indirect Determination of Adenosine Antagonism Via Gene Expression

Cells of the permanent line CHO K1 (Chinese Hamster Ovary) are stably transfected with a reporter construct (CRE luciferase) and the cDNA for the adenosine receptor subtype A2a or A2b. A2a or A2b receptors are coupled via Gas proteins to the adenylate cyclase. Through receptor activation, the adenylate cyclase is activated and therefore the cAMP level in the cell increases. Via the reporter construct, a cAMP-dependent promoter, the change in the cAMP level is coupled to luciferase expression.

For determination of adenosine antagonism on the adenosine receptor subtype A1, once again CHO K1 cells are stably transfected, but this time with a $Ca^{2+}$-sensitive reporter construct (NFAT-TA-Luc; Clontech) and an A1-Gα16 fusion construct. This receptor chimera is, in contrast to the native A1 receptor (Gαi-coupling), coupled to the phospholipase C. The luciferase is expressed here as a function of the cytosolic $Ca^{2+}$ concentration.

The permanent cell lines are cultured in DMEM/F12 (Cat. No. BE04-687Q; BioWhittaker) with 10% FCS (fetal calf serum) and various additives (20 ml/liter 1M HEPES (Cat. No. 15630; Gibco), 20 ml/liter GlutaMAX (Cat. No. 35050-038, Gibco), 14 ml/liter MEM sodium pyruvate (Cat. No. 11360-039; Gibco) 10 ml/liter PenStrep (Cat. No. 15070-063; Gibco)) at 37° C. under 5% carbon dioxide, and split twice weekly.

For testing in the 384-well plate format, the cells are sown at 2000 cells/well in 25 µl/well sowing medium and cultured at 37° C. under 5% carbon dioxide until substance testing. The A2a and A2b cells are sown, 24 h before substance testing, in medium with additives and 5% FCS, the base medium used for the A2a cells being DMEM/F12 and the base medium used for the A2b cells being OptiMEM (Cat. No. 31985-047; Gibco). The A1-Gα16 cells are sown, 48 h before substance testing, in OptiMEM with 2.5% dialysed FCS and additives. On the day of the test, prior to the addition of the substance, the medium is replaced by 25 µl of Cafty buffer (Cat. No. T21-154; PAA) with 2 mM calcium chloride and 0.1% BSA (bovine serum albumin) Dilution series in Cafty buffer with 2 mM calcium chloride and 0.1% BSA (bovine serum albumin) and a suitable agonist concentration are prepared from the substances to be tested, which are dissolved in DMSO. The substances are pipetted at a final concentration of from $5\times10^{-5}$ M to $2.56\times10^{-11}$ M to the test cultures, while the DMSO content on the cells should not exceed 0.5%. NECA (5-N-ethyl carboxamidoadenosine) at a final concentration of 30 nM, which roughly corresponds to the $EC_{50}$ concentration, is used as agonist for the A2a and A2b cells. 25 nM CPA (N6-cyclopentyladenosine), which roughly corresponds to the $EC_{75}$ concentration, is used as agonist for the A1-Gα16 cells. After adding the substances, the cell plates are incubated for 3-4 h at 37° C. under 5% carbon dioxide. Then, 25 μl of a solution consisting to 50% of lysis reagent (30 nM disodium hydrogen phosphate, 10% glycerol, 3% Triton X-100, 25 mM TrisHCl, 2 mM dithiothreitol (DTT), pH 7.8) and to 50% of luciferase substrate solution (2.5 mM ATP, 0.5 mM luciferin, 0.1 mM coenzyme A, 10 mM tricin, 1.35 mM magnesium sulphate, 15 mM DTT, pH 7.8) are added to the cells directly before measurement. The luciferase activity is detected with a luminescence reader. The $IC_{50}$ values are determined, i.e. the concentration at which the luciferase response, produced by the respective agonist, is inhibited to 50%. ZM241385, for the A2a and A2b cells, and DPCPX (1,3-dipropyl-8-cyclopentylxanthine), for the A1-Gα16 cells, are used as reference antagonist.

B-6. Determination of Pharmacokinetic Parameters after Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC (area under the concentration-time curve), $C_{max}$ (maximum plasma concentration), $T_{1/2}$ (half-life) and CL (clearance) by means of a validated pharmacokinetic computer program.

B-7. Determination of the Solubility

Reagents Required:
PBS buffer pH 6.5: 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N aqueous sodium hydroxide solution (for example from Bernd Kraft GmbH, Art. No. 01030.4000) are weighed into a 1 liter measuring flask, the flask is filled with distilled water to 1 liter and the mixture is stirred for 1 hour. Using 1 N hydrochloric acid (for example from Merck, Art. No. 1.09057.1000) the pH is then adjusted to 6.5.

PEG/water solution (70:30 v/v): 70 ml of polyethylene glycol 400 (for example from Merck, Art. No. 8.17003.1000) and 30 ml of distilled water are homogenized in a 100 ml measuring flask.

PEG/PBS buffer pH 6.5 (20:80 v/v): 20 ml of polyethylene glycol 400 (for example from Merck, Art. No. 8.17003.1000) and 80 ml of PBS buffer pH 6.5 are homogenized in a 100 ml measuring flask.

Dimethyl sulphoxide (for example from Baker, Art. No. 7157.2500)

Distilled water.

Preparation of the Starting Solution (Original Solution):
At least 4 mg of the test substance are weighed accurately into a wide-necked 10 mm screw V vial (from Glastechnik Gräfenroda GmbH, Art. No. 8004-WM-H/V15μ) with fitting screw cap and septum, in a pipetting robot DMSO is added to a concentration of 50 mg/ml and the mixture is shaken for 10 minutes.

Preparation of the Calibration Solutions:
Preparation of the starting solution for calibration solutions (stock solution): With the aid of a pipetting robot, 10 μl of the original solution are transferred into a microtiter plate and made up with DMSO to a concentration of 600 μg/ml. The sample is shaken until everything has gone into solution.

Calibration solution 1 (20 μg/ml): 1000 μl of DMSO are added to 34.4 μl of the stock solution, and the mixture is homogenized.

Calibration solution 2 (2.5 μg/ml): 700 μl of DMSO are added to 100 μl of calibration solution 1, and the mixture is homogenized.

Preparation of the Sample Solutions:
Sample solution for solubilities of up to 5 g/liter in PBS buffer pH 6.5: 10 μl of the original solution are transferred into a microtiter plate, and 1000 μl of PBS buffer pH 6.5 are added.

Sample solution for solubilities of up to 5 g/liter in PEG/water (70:30): 10 μl of the original solution are transferred into a microtiter plate, and 1000 μl of PEG/water (70:30) are added.

Sample solution for solubilities of up to 5 g/liter in PEG/PBS buffer pH 6.5 (20:80): 10 μl of the original solution are transferred into a microtiter plate, and 1000 μl of PEG/PBS buffer pH 6.5 (20:80) are added.

Practice:
The sample solutions prepared in this manner are shaken at 1400 rpm in a temperature-adjustable shaker (for example Eppendorf Thermomixer comfort Art. No. 5355 000.011 with interchangeable block Art. No. 5362.000.019) at 20° C. for 24 hours. In each case 180 μl are taken from these solutions and transferred into Beckman Polyallomer Centrifuge Tubes (Art. No. 343621). These solutions are centrifuged at about 223 000×g for one hour (for example Beckman Optima L-90K Ultracentrifuge with Type 42.2 Ti Rotor at 42 000 rpm). From each of the sample solutions, 100 μl of the supernatant are removed and diluted 1:5 and 1:100 with DMSO. From each dilution, a sample is transferred into a vessel suitable for HPLC analysis.

Analysis:
The samples are analysed by RP-HPLC. Quantification is carried out using a two-point calibration curve of the test compound in DMSO. The solubility is expressed in mg/liter. Analysis sequence: 1) calibration solution 2.5 mg/ml; 2) calibration solution 20 μg/ml; 3) sample solution 1:5; 4) sample solution 1:100.

HPLC Method for Acids:
Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5μ; temperature: 40° C.; mobile phase A: water/phosphoric acid pH 2; mobile phase B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:
Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5μ; temperature: 30° C.; mobile phase A: water+5 ml of perchloric acid/liter; mobile phase B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

B-8. Determination of the Metabolic Stability

To determine the metabolic stability of test compounds, the latter are incubated in vitro with liver microsomes or, preferably, with primary fresh hepatocytes of various animal species (for example from rat and dog) and also of human origin to obtain and to compare metabolite profiles of a hepatic phase I and phase II metabolism which is as complete as possible.

The test compounds are incubated at a concentration of 10-20 μM. To this end, stock solutions of the substances at a concentration of 1-2 mM in acetonitrile are prepared and then pipetted at a dilution of 1:100 into the incubation mixture. The liver microsomes are incubated at 37° C. in 50 mM potassium phosphate buffer (pH 7.4) with and without NADPH-generating system consisting of 1 mM $NADP^+$, 10 mM glucose 6-phosphate and 1 unit of glucose 6-phosphate dehydrogenase. Primary hepatocytes are also incubated at 37° C. in suspension in Williams E medium. After an incubation time of 0-4 hours, the incubation mixtures are quenched with acetonitrile (final concentration about 30%) and the protein is centrifuged off at about 15 000×g. The samples quenched in this manner are either analyzed directly or stored at −20° C. until analysis.

Analysis is carried out using high-performance liquid chromatography with ultraviolet and mass-spectrometric detection (HPLC-UV-MS/MS). To this end, the supernatants of the incubation samples are chromatographed using suitable C18 reversed-phase columns and variable mobile phase mixtures of acetonitrile and 10 mM aqueous ammonium formate solution. The UV chromatograms in combination with mass-spectrometric MS/MS data serve to identify the metabolites and to elucidate their structures.

C. WORKING EXAMPLES OF PHARMACEUTICAL COMPOSITIONS

The compounds of the invention can be converted into pharmaceutical preparations in the following ways:
Tablet:
Composition:
100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.
Tablet weight 212 mg, diameter 8 mm, radius of curvature 12 mm.
Production:
The mixture of compound of the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.
Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.
10 ml of oral suspension correspond to a single dose of 100 mg of the compound of the invention.
Production:
The Rhodigel is suspended in ethanol, and the compound of the invention is added to the suspension. The water is added while stirring. The mixture is stirred for about 6 h until the swelling of the Rhodigel is complete.
Solution which can be Administered Orally:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring process is continued until the compound of the invention has completely dissolved.
i.v. Solution:
The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:
1. A compound of the formula (I)

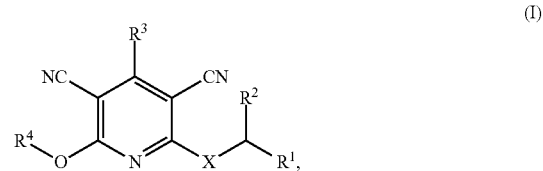

in which
X represents O or S,
$R^1$ represents oxazolyl,
where oxazolyl may be substituted by 1 or 2 substituents independently of one another selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, hydroxycarbonyl, $(C_1-C_6)$-alkoxycarbonyl, aminocarbonyl, mono-$(C_1-C_6)$-alkylaminocarbonyl, di-$(C_1-C_6)$-alkylaminocarbonyl, $(C_3-C_7)$-cycloalkylaminocarbonyl, aminosulphonyl, mono-$(C_1-C_6)$-alkylaminosulphonyl, di-$(C_1-C_6)$-alkylaminosulphonyl, $(C_1-C_6)$-alkylsulphonylamino, and -L-$R^5$,
in which
L represents a bond, NH or O,
$R^5$ represents phenyl,
where phenyl for its part may be substituted by 1 to 3 substituents independently of one another selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, hydroxycarbonyl and $(C_1-C_6)$-alkoxycarbonyl,
$R^2$ represents hydrogen or $(C_1-C_4)$-alkyl,
$R^3$ represents phenyl,
where phenyl may be substituted by 1 to 3 substituents independently of one another selected from the group consisting of halogen, cyano, hydroxyl, $(C_1-C_6)$-alkyl, $(C_1-C_6)$-alkoxy, $(C_3-C_7)$-cycloalkoxy, and —$NR^4R^B$,
where $(C_1-C_6)$-alkyl and $(C_1-C_6)$-alkoxy may be substituted by 1 to 3 substituents independently of one another selected from the group consisting of fluorine, trifluoromethyl, $(C_3-C_7)$-cycloalkyl, hydroxyl, $(C_1-C_4)$-alkoxy, hydroxycarbonyl, ($C_1$-$C_4$)-alkoxycarbonyl, amino, aminocarbonyl, mono-($C_1$-$C_4$)-alkylamino and di-($C_1$-$C_4$)-alkylamino,
and
where ($C_3$-$C_7$)-cycloalkoxy may be substituted by 1 or 2 substituents independently of one another selected from the group consisting of ($C_1$-$C_4$)-alkyl, hydroxyl, oxo and ($C_1$-$C_4$)-alkoxy,
and
in which
$R^A$ represents hydrogen or ($C_1$-$C_6$)-alkyl,
where ($C_1$-$C_6$)-alkyl for its part may be substituted by 1 to 3 fluorine substituents,
and
where ($C_1$-$C_6$)-alkyl for its part may be substituted by a substituent selected from the group consisting of hydroxyl and ($C_1$-$C_4$)-alkoxy,
$R^B$ represents hydrogen, ($C_1$-$C_6$)-alkyl, ($C_3$-$C_7$)-cycloalkyl, ($C_1$-$C_6$)-alkylcarbonyl, ($C_1$-$C_4$)-alkylsulphonyl or ($C_3$-$C_7$)-cycloalkylsulphonyl,
where ($C_1$-$C_6$)-alkyl for its part may be substituted by 1 or 2 substituents independently of one another selected from the group consisting of fluorine, trifluoromethyl, ($C_3$-$C_7$)-cycloalkyl, hydroxyl, ($C_1$-$C_4$)-alkoxy, hydroxycarbonyl, ($C_1$-$C_4$)-alkoxycarbonyl, amino, mono-($C_1$-$C_4$)-alkylamino and di-($C_1$-$C_4$)-alkylamino,
and
where ($C_3$-$C_7$)-cycloalkyl for its part may be substituted by 1 or 2 substituents independently of one another selected from the group consisting of ($C_1$-$C_4$)-alkyl, hydroxyl, oxo and ($C_1$-$C_4$)-alkoxy,
$R^4$ represents ($C_1$-$C_6$)-alkyl or ($C_3$-$C_7$)-cycloalkyl,
where ($C_1$-$C_6$)-alkyl may be substituted by 1 or 2 substituents independently of one another selected from the group consisting of fluorine, trifluoromethyl, ($C_3$-$C_7$)-cycloalkyl, hydroxyl, ($C_1$-$C_4$)-alkoxy, hydroxycarbonyl, ($C_1$-$C_4$)-alkoxycarbonyl, amino, mono-($C_1$-$C_4$)-alkylamino, di-($C_1$-$C_4$)-alkylamino, aminocarbonyl, mono-($C_1$-$C_4$)-alkylaminocarbonyl, and di-($C_1$-$C_4$)-alkylaminocarbonyl,
where ($C_1$-$C_4$)-alkoxy may be substituted by 1 or 2 substituents independently of one another selected from the group consisting of hydroxyl and ($C_1$-$C_4$)-alkoxy
and
where ($C_3$-$C_7$)-cycloalkyl and 4- to 6-membered heterocyclyl may be substituted by 1 or 2 substituents independently of one another selected from the group consisting of ($C_1$-$C_4$)-alkyl, hydroxyl, ($C_1$-$C_4$)-alkoxy, hydroxycarbonyl, ($C_1$-$C_4$)-alkoxycarbonyl, amino, mono-($C_1$-$C_4$)-alkylamino and di-($C_1$-$C_4$)-alkylamino,
and a salt thereof.

2. The compound of claim 1 in which
X represents S,
$R^1$ represents oxazolyl, where oxazolyl may be substituted by 1 or 2 substituents independently of one another selected from the group consisting of fluorine, chlorine, cyano, ($C_1$-$C_4$)-alkyl, trifluoromethyl, ($C_1$-$C_4$)-alkoxy, amino, mono-($C_1$-$C_4$)-alkylamino, di-($C_1$-$C_4$)-alkylamino, hydroxycarbonyl, ($C_1$-$C_4$)-alkoxycarbonyl, aminocarbonyl, mono-($C_1$-$C_4$)-alkylaminocarbonyl, di-($C_1$-$C_4$)-alkylaminocarbonyl, ($C_3$-$C_6$)-cycloalkylaminocarbonyl, ($C_1$-$C_4$)-alkylsulphonylamino, and -L-$R^5$,
in which
L represents a bond or NH,
$R^5$ represents phenyl,
where phenyl for its part may be substituted by 1 or 2 substituents independently of one another selected from the group consisting of fluorine, chlorine, cyano, ($C_1$-$C_4$)-alkyl, trifluoromethyl, ($C_1$-$C_4$)-alkoxy, trifluoromethoxy, amino, hydroxycarbonyl and ($C_1$-$C_4$)-alkoxycarbonyl,
$R^2$ represents hydrogen or methyl,
$R^3$ represents phenyl
where phenyl may be substituted by 1 or 2 substituents independently of one another selected from the group consisting of fluorine, ($C_1$-$C_6$)-alkyl, hydroxyl, ($C_1$-$C_4$)-alkoxy and —$NR^A R^B$,
where ($C_1$-$C_6$)-alkyl and ($C_1$-$C_4$)-alkoxy may be substituted by 1 to 3 substituents independently of one another selected from the group consisting of fluorine, trifluoromethyl, hydroxyl, methoxy, ethoxy, hydroxycarbonyl, amino, methylamino, ethylamino, NN-dimethylamino and NN-diethylamino,
and
in which
$R^A$ represents hydrogen or ($C_1$-$C_4$)-alkyl,
where ($C_1$-$C_4$)-alkyl for its part may be substituted by a substituent selected from the group consisting of hydroxyl and ($C_1$-$C_4$)-alkoxy,
$R^B$ represents hydrogen or ($C_1$-$C_4$)-alkyl,
where ($C_1$-$C_4$)-alkyl for its part may be substituted by 1 or 2 substituents independently of one another selected from the group consisting of hydroxyl, ($C_1$-$C_4$)-alkoxy and hydroxycarbonyl,
$R^4$ represents ($C_1$-$C_6$)-alkyor, ($C_4$-$C_6$)-cycloalkyl,
where ($C_1$-$C_6$)-alkyl may be substituted by 1 or 2 substituents independently of one another selected from the group consisting of fluorine, trifluoromethyl, ($C_3$-$C_7$)-cycloalkyl, hydroxyl, methoxy, ethoxy, hydroxycarbonyl, methoxycarbonyl, ethoxycarbonyl, amino, methylamino, ethylamino, N,N-dimethylamino, and N,N-diethylamino,
where ($C_3$-$C_7$)-cycloalkyl and 5- or 6-membered heterocyclyl may be substituted by 1 or 2 substituents independently of one another selected from the group consisting of methyl, hydroxyl, methoxy, hydroxycarbonyl, methoxycarbonyl, ethoxycarbonyl, amino, methylamino and N,N-dimethylamino,
and a salt thereof.

3. The compound of claim 1 in which
X represents O or S,
$R^1$ represents oxazolyl,
where oxazolyl is substituted by a -L-$R^5$ substituent,
in which
L represents a bond or NH,
$R^5$ represents phenyl,
where phenyl for its part may be substituted by 1 or 2 substituents independently of one another selected from the group consisting of fluorine, chlorine, methyl, methoxy, ethoxy, hydroxycarbonyl, methoxycarbonyl and ethoxycarbonyl,
and
where oxazolyl may be substituted by a substituent selected from the group consisting of fluorine, methyl, ethyl, methoxy, hydroxycarbonyl and methoxycarbonyl,
$R^2$ represents hydrogen or methyl,
$R^3$ represents phenyl, where phenyl, may be substituted by 1 or 2 substituents independently of one another selected from the group consisting of fluorine, $(C_1$-$C_6)$-alkyl, hydroxyl, $(C_1$-$C_4)$-alkoxy and —$NR^AR^B$,
  where $(C_1$-$C_6)$-alkyl and $(C_1$-$C_4)$-alkoxy may be substituted by 1 to 3 substituents independently of one another selected from the group consisting of fluorine, trifluoromethyl, hydroxyl, methoxy, ethoxy, hydroxycarbonyl, amino, methylamino, ethylamino, N,N-dimethylamino and N,N-diethylamino,
and
in which
  $R^A$ represents hydrogen or $(C_1$-$C_4)$-alkyl,
    where $(C_1$-$C_4)$-alkyl for its part may be substituted by a substituent selected from the group consisting of hydroxyl and $(C_1$-$C_4)$-alkoxy,
  $R^B$ represents hydrogen or $(C_1$-$C_4)$-alkyl,
    where $(C_1$-$C_4)$-alkyl for its part may be substituted by 1 or 2 substituents independently of one another selected from the group consisting of hydroxyl, $(C_1$-$C_4)$-alkoxy and hydroxycarbonyl,
$R^4$ represents $(C_1$-$C_6)$-alkyl or $(C_4$-$C_6)$-cycloalkyl,
  where $(C_1$-$C_6)$-alkyl may be substituted by 1 or 2 substituents independently of one another selected from the group consisting of fluorine, trifluoromethyl, $(C_3$-$C_7)$-cycloalkyl, hydroxyl, methoxy and ethoxy,
  and
  where $(C_4$-$C_6)$-cycloalkyl may be substituted by 1 or 2 substituents independently of one another selected from the group consisting of methyl, hydroxyl and methoxy,
and a salt thereof.

4. The compound of claim 1 in which
X represents S,
$R^1$ represents oxazolyl,
  where oxazolyl is substituted by a -L-$R^5$ substituent,
    in which
    L represents a bond or NH,
    $R^5$ represents phenyl,
      where phenyl for its part may be substituted by 1 or 2 substituents independently of one another selected from the group consisting of fluorine, chlorine, methyl, methoxy, ethoxy, hydroxycarbonyl, methoxycarbonyl and ethoxycarbonyl,
  and
  where oxazolyl may be substituted by a substituent selected from the group consisting of fluorine, methyl, ethyl, methoxy, hydroxycarbonyl and methoxycarbonyl,
$R^2$ represents hydrogen,
$R^3$ represents phenyl,
  where phenyl may be substituted by 1 or 2 substituents independently of one another selected from the group consisting of $(C_1$-$C_6)$-alkyl, hydroxyl and $(C_1$-$C_4)$-alkoxy,
    where $(C_1$-$C_6)$-alkyl and $(C_2$-$C_4)$-alkoxy may be substituted by 1 or 2 substituents independently of one another selected from the group consisting of hydroxyl and methoxy,
$R^4$ represents $(C_1$-$C_4)$-alkyl,
  where alkyl may be substituted by 1 or 2 hydroxyl substituents,
and a salt thereof.

5. A process for preparing a compound of the formula (I) as defined in claim 1, wherein

[A] reacting a compound of the formula (II-A)

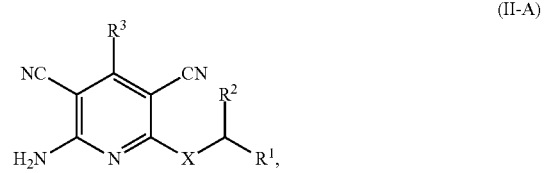
(II-A)

in which X, $R^1$, $R^2$ and $R^3$ each have the meanings given in claim 1, with copper(II) chloride and isoamyl nitrate in a solvent, thereby producing a compound of the formula (III-A)

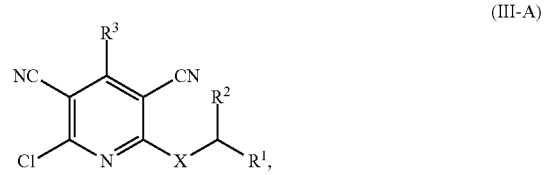
(III-A)

reacting the compound of formula (III-A) in an inert solvent in the presence of a base with a compound of the formula (IV)

$R^4$—OH         (IV), in which $R^4$ has the meaning given in claim 1, or

[B] in the case that X represents S, reacting a compound of the formula (II-B)

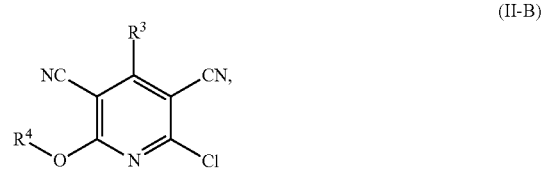
(II-B)

in which $R^3$ and $R^4$ each have the meanings given in claim 1, in an inert solvent with an alkali metal sulphide, thereby producing a compound of the formula (III-B)

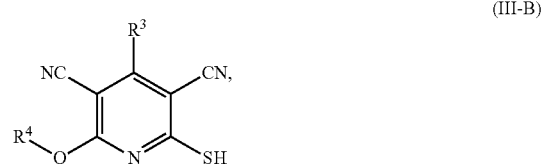
(III-B)

reacting the compound of formula (III-B) in an inert solvent in the presence of a base with a compound of the formula (V)

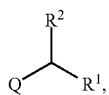
(V)

in which $R^1$ and $R^2$ each have the meanings given in claim 1 and

Q represents a leaving group, removing any protective groups present to provide the compound of the formula (I), and optionally reacting the compound of formula (I) with a base or acid thereby producing a salt thereof.

6. A pharmaceutical composition comprising a compound of claim 1 in combination with an inert nontoxic pharmaceutically suitable auxiliary.

7. The method of claim 5, wherein Q represents halogen, mesylate, tosylate or triflate.

8. The compound according to claim 1, named 2-({[2-(4-chlorophenyl)-1,3-oxazol-4-yl]methyl}sulphanyl)-4-[4-(2-hydroxyethoxyl)phenyl]-6-methoxypyridine-3,5-dicarbonitrile and having the formula

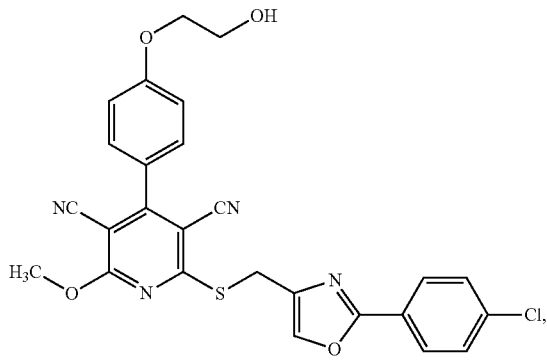 [SMILES: COc1nc(SCc2coc(-c3ccc(Cl)cc3)n2)c(C#N)c(-c2ccc(OCCO)cc2)c1C#N]

* * * * *